US00RE50004E

(19) United States
(12) Reissued Patent
Buckberry

(10) Patent Number: US RE50,004 E
(45) Date of Reissued Patent: Jun. 11, 2024

(54) DUAL HAEMODIALYSIS AND HAEMODIAFILTRATION BLOOD TREATMENT DEVICE

(71) Applicant: Quanta Dialysis Technologies Ltd., Warwickshire (GB)

(72) Inventor: Clive Henry Buckberry, Warwickshire (GB)

(73) Assignee: QUANTA DIALYSIS TECHNOLOGIES LTD., Warwickshire (GB)

(21) Appl. No.: 17/345,754

(22) Filed: Jun. 11, 2021

Related U.S. Patent Documents

Reissue of:
(64) Patent No.: 10,314,959
Issued: Jun. 11, 2019
Appl. No.: 14/911,846
PCT Filed: Aug. 13, 2014
PCT No.: PCT/GB2014/052486
§ 371 (c)(1),
(2) Date: Feb. 12, 2016
PCT Pub. No.: WO2015/022537
PCT Pub. Date: Feb. 19, 2015

(30) Foreign Application Priority Data

Aug. 14, 2013 (GB) ..... 1314512

(51) Int. Cl.
*A61M 1/16* (2006.01)
*A61M 1/14* (2006.01)
(Continued)

(52) U.S. Cl.
CPC ..... *A61M 1/168* (2013.01); *A61M 1/154* (2022.05); *A61M 1/155* (2022.05); *A61M 1/156* (2022.05);
(Continued)

(58) Field of Classification Search
CPC ..... A61M 1/168; A61M 1/154; A61M 1/155; A61M 1/156; A61M 1/1562;
(Continued)

(56) References Cited

U.S. PATENT DOCUMENTS 2,696,173 A 12/1954 Thormod
3,338,171 A 8/1967 Conklin et al.
(Continued)

FOREIGN PATENT DOCUMENTS

CA 81430 8/1997
DE 10024447 A1 11/2001
(Continued)

OTHER PUBLICATIONS

Ergo-Express Motorized Dialysis Cart, Aug. 14, 2017, youtube.com [online], [site visited Jan. 9, 2022], Available from internet, URL: <https://www.youtube.com/watch?v=j4rAXthOmbY> (Year: 2017).
(Continued)

*Primary Examiner* — Norca L. Torres Velazquez
(74) *Attorney, Agent, or Firm* — The Marbury Law Group, PLLC

(57) ABSTRACT

The invention relates to a blood treatment device, in particular a device which can perform haemodialysis and haemodifiltration procedures. This is achieved using an interconnected pump and valve arrangement which can be controlled to direct fluid across a dialysis membrane or parallel to said membrane depending on the type of processing required. This allows dynamic variation between modes of operation and treatment.

45 Claims, 4 Drawing Sheets

(51) Int. Cl.
*A61M 1/34* (2006.01)
*A61M 1/36* (2006.01)

(52) U.S. Cl.
CPC ..... *A61M 1/1562* (2022.05); *A61M 1/15632* (2022.05); *A61M 1/1565* (2022.05); *A61M 1/16* (2013.01); *A61M 1/1645* (2014.02); *A61M 1/34* (2013.01); *A61M 1/3413* (2013.01); *A61M 1/342* (2013.01); *A61M 1/3635* (2014.02); *A61M 1/1566* (2022.05); *A61M 2202/0413* (2013.01); *A61M 2205/128* (2013.01); *A61M 2205/33* (2013.01)

(58) Field of Classification Search
CPC .. A61M 1/15632; A61M 1/1565; A61M 1/16; A61M 1/1645; A61M 1/34; A61M 1/3413; A61M 1/342; A61M 1/3635
See application file for complete search history.

(56) References Cited

U.S. PATENT DOCUMENTS

| | | | |
|---|---|---|---|
| 3,468,261 | A | 9/1969 | Schmierer |
| 3,605,566 | A | 9/1971 | Vetter |
| 3,606,592 | A | 9/1971 | Madurski et al. |
| 3,753,493 | A | 8/1973 | Mellor |
| 3,774,762 | A | 11/1973 | Lichtenstein |
| 3,807,906 | A | 4/1974 | Breit |
| 3,921,622 | A | 11/1975 | Cole |
| 3,972,320 | A | 8/1976 | Kalman |
| 4,070,725 | A | 1/1978 | Cornelius |
| 4,142,845 | A | 3/1979 | Lepp et al. |
| 4,161,264 | A | 7/1979 | Malmgren |
| 4,205,686 | A | 6/1980 | Harris et al. |
| 4,353,990 | A | 10/1982 | Manske et al. |
| 4,366,061 | A | 12/1982 | Papanek et al. |
| 4,368,261 | A | 1/1983 | Klose et al. |
| 4,370,983 | A | 2/1983 | Lichtenstein |
| 4,430,048 | A | 2/1984 | Fritsch |
| 4,494,912 | A | 1/1985 | Pauliukonis |
| D277,991 | S | 3/1985 | Becker |
| 4,534,755 | A | 8/1985 | Calvert et al. |
| 4,534,756 | A | 8/1985 | Nelson |
| 4,546,669 | A | 10/1985 | Fischer et al. |
| 4,564,342 | A | 1/1986 | Weber et al. |
| 4,599,165 | A | 7/1986 | Chevallet |
| 4,648,869 | A | 3/1987 | Bobo, Jr. |
| 4,666,598 | A | 5/1987 | Heath et al. |
| 4,710,163 | A | 12/1987 | Butterfield |
| 4,771,792 | A | 9/1988 | Seale |
| 4,828,543 | A | 5/1989 | Weiss et al. |
| 4,897,184 | A | 1/1990 | Shouldice et al. |
| D308,249 | S | 5/1990 | Buckley |
| 4,969,991 | A | 11/1990 | Valadez |
| 5,000,664 | A | 3/1991 | Lawless et al. |
| 5,012,197 | A | 4/1991 | Seiffert et al. |
| 5,032,265 | A | 7/1991 | Jha et al. |
| 5,055,198 | A | 10/1991 | Shettigar |
| 5,095,910 | A | 3/1992 | Powers |
| 5,103,211 | A | 4/1992 | Daoud et al. |
| 5,126,831 | A | 6/1992 | Nakagawara |
| 5,232,434 | A | 8/1993 | Inagaki et al. |
| 5,252,213 | A | 10/1993 | Ahmad et al. |
| D341,890 | S | 11/1993 | Sievert et al. |
| D344,339 | S | 2/1994 | Yoshikawa et al. |
| 5,304,349 | A | 4/1994 | Polaschegg |
| D347,896 | S | 6/1994 | Dickinson et al. |
| D351,470 | S | 10/1994 | Scherer et al. |
| 5,385,540 | A | 1/1995 | Abbott et al. |
| 5,421,823 | A | 6/1995 | Kamen et al. |
| 5,458,468 | A | 10/1995 | Ye et al. |
| 5,476,368 | A | 12/1995 | Rabenau et al. |
| 5,476,792 | A | 12/1995 | Ezrielev et al. |
| D370,979 | S | 6/1996 | Pascale et al. |
| 5,558,347 | A | 9/1996 | Nicholson |
| 5,586,872 | A | 12/1996 | Skobelev et al. |
| 5,586,873 | A | 12/1996 | Novak et al. |
| 5,591,344 | A | 1/1997 | Kenley et al. |
| 5,643,201 | A | 7/1997 | Peabody et al. |
| 5,650,071 | A | 7/1997 | Brugger et al. |
| 5,653,456 | A | 8/1997 | Mough |
| 5,658,456 | A | 8/1997 | Kenley et al. |
| 5,665,307 | A | 9/1997 | Kirschner et al. |
| 5,727,550 | A | 3/1998 | Montecalvo |
| D395,085 | S | 6/1998 | Kenley et al. |
| 5,788,851 | A | 8/1998 | Kenley et al. |
| 5,807,322 | A | 9/1998 | Lindsey et al. |
| 5,882,300 | A | 3/1999 | Malinouskas et al. |
| 5,948,247 | A | 9/1999 | Gillerfalk et al. |
| 5,957,670 | A | 9/1999 | Duncan et al. |
| 5,995,910 | A | 11/1999 | Discenzo |
| 6,077,443 | A | 6/2000 | Goldau |
| 6,126,831 | A | 10/2000 | Goldau et al. |
| 6,132,378 | A | 10/2000 | Marino |
| 6,143,181 | A | 11/2000 | Falkvall et al. |
| 6,153,102 | A | 11/2000 | Kenley et al. |
| 6,216,029 | B1 | 4/2001 | Paltieli |
| 6,218,329 | B1 | 4/2001 | Singh et al. |
| 6,251,279 | B1 | 6/2001 | Peterson et al. |
| 6,261,065 | B1 | 7/2001 | Nayak et al. |
| 6,303,036 | B1 | 10/2001 | Collins et al. |
| 6,382,923 | B1 | 5/2002 | Gray |
| 6,514,462 | B1 | 2/2003 | Simons |
| 6,558,347 | B1 | 5/2003 | Jhuboo et al. |
| 6,582,206 | B2 | 6/2003 | Schluecker |
| 6,626,832 | B1 | 9/2003 | Paltieli et al. |
| 6,626,878 | B1 | 9/2003 | Leisner et al. |
| 6,645,176 | B1 | 11/2003 | Christenson et al. |
| 6,663,829 | B1 | 12/2003 | Kjellstrand |
| 6,733,476 | B2 | 5/2004 | Christenson et al. |
| 6,743,204 | B2 | 6/2004 | Christenson et al. |
| 6,801,646 | B1 | 10/2004 | Pena et al. |
| 6,814,547 | B2 | 11/2004 | Childers et al. |
| 6,967,002 | B1 | 11/2005 | Edgson et al. |
| 7,040,142 | B2 | 5/2006 | Burbank |
| 7,107,837 | B2 | 9/2006 | Lauman et al. |
| 7,153,286 | B2 | 12/2006 | Busby et al. |
| 7,220,358 | B2 | 5/2007 | Schacht et al. |
| 7,284,964 | B2 | 10/2007 | McDowell et al. |
| 7,383,721 | B2 | 6/2008 | Parsons et al. |
| 7,434,312 | B2 | 10/2008 | Christenson et al. |
| 7,494,590 | B2 | 2/2009 | Felding et al. |
| 7,604,398 | B1 | 10/2009 | Akers et al. |
| 7,648,627 | B2 | 1/2010 | Beden et al. |
| 7,857,976 | B2 | 12/2010 | Bissler et al. |
| 7,874,999 | B2 | 1/2011 | Busby |
| 7,896,197 | B2 | 3/2011 | Furey et al. |
| D641,882 | S | 7/2011 | Hickey et al. |
| 8,114,043 | B2 | 2/2012 | Muller |
| 8,132,388 | B2 | 3/2012 | Nagy et al. |
| 8,137,184 | B2 | 3/2012 | Ajiro et al. |
| 8,137,300 | B2 | 3/2012 | Han et al. |
| 8,167,431 | B2 | 5/2012 | DeCusatis et al. |
| 8,187,184 | B2 | 5/2012 | Muller et al. |
| 8,192,388 | B2 | 6/2012 | Hogard |
| 8,197,431 | B2 | 6/2012 | Bennison |
| 8,221,320 | B2 | 7/2012 | Bouton |
| 8,348,850 | B2 | 1/2013 | Frinak et al. |
| 8,360,977 | B2 | 1/2013 | Marttila et al. |
| 8,529,490 | B2 | 9/2013 | Wariar et al. |
| 8,535,522 | B2 | 9/2013 | Fulkerson et al. |
| 8,535,525 | B2 | 9/2013 | Heyes et al. |
| D693,469 | S | 11/2013 | Chung et al. |
| 8,597,505 | B2 | 12/2013 | Fulkerson et al. |
| D702,842 | S | 4/2014 | Hyde et al. |
| 8,685,244 | B2 | 4/2014 | Heyes et al. |
| 8,696,571 | B2 | 4/2014 | Marttila et al. |
| 8,708,908 | B2 | 4/2014 | Bouton |
| 8,708,946 | B2 | 4/2014 | Han et al. |
| D705,432 | S | 5/2014 | Lura et al. |
| 8,798,908 | B2 | 8/2014 | Bourdeaut |
| 8,801,646 | B2 | 8/2014 | Han et al. |
| D714,454 | S | 9/2014 | Amemiya et al. |
| D714,946 | S | 10/2014 | Lura et al. |

(56) References Cited

U.S. PATENT DOCUMENTS

| | | | |
|---|---|---|---|
| 8,926,544 | B2 | 1/2015 | Hogard et al. |
| D724,740 | S | 3/2015 | Collins et al. |
| 8,974,394 | B2 | 3/2015 | Frinak et al. |
| 9,011,334 | B2 | 4/2015 | Bouton |
| D735,868 | S | 8/2015 | Mareguddi et al. |
| 9,220,825 | B2 | 12/2015 | Buckberry |
| D781,410 | S | 3/2017 | Ritter et al. |
| 9,744,285 | B2 | 8/2017 | Heyes et al. |
| 9,833,553 | B2 | 12/2017 | Higgitt et al. |
| 10,314,962 | B2 | 6/2019 | Buckberry |
| 10,456,516 | B2 | 10/2019 | Heyes et al. |
| D867,597 | S | 11/2019 | Bauer et al. |
| 10,543,305 | B2 | 1/2020 | Buckberry et al. |
| D879,967 | S | 3/2020 | Verguldi et al. |
| D907,211 | S | 1/2021 | Spurling |
| 10,881,775 | B2 | 1/2021 | Wallace |
| 10,960,120 | B2 | 3/2021 | Wallace et al. |
| D924,410 | S | 7/2021 | Mendoza et al. |
| D938,046 | S | 12/2021 | Gupta et al. |
| 11,365,728 | B2 | 6/2022 | Westenbrink |
| 11,571,499 | B2 | 2/2023 | Milad et al. |
| 11,583,618 | B2 | 2/2023 | Buckberry et al. |
| 2003/0217962 | A1 | 11/2003 | Childers et al. |
| 2004/0195157 | A1 | 10/2004 | Mullins et al. |
| 2004/0206703 | A1 | 10/2004 | Bosetto et al. |
| 2004/0215129 | A1 | 10/2004 | Edgson et al. |
| 2004/0223857 | A1 | 11/2004 | Kline |
| 2005/0020961 | A1 | 1/2005 | Burbank et al. |
| 2005/0205476 | A1 | 9/2005 | Chevallet et al. |
| 2005/0209547 | A1 | 9/2005 | Burbank et al. |
| 2005/0234384 | A1 | 10/2005 | Westberg |
| 2006/0121623 | A1 | 6/2006 | He et al. |
| 2007/0083193 | A1 | 4/2007 | Werneth et al. |
| 2008/0006089 | A1 | 1/2008 | Adnan et al. |
| 2008/0200865 | A1 | 8/2008 | Bedingfield |
| 2008/0283096 | A1 | 11/2008 | Scheringer et al. |
| 2009/0007642 | A1 | 1/2009 | Busby et al. |
| 2009/0009290 | A1 | 1/2009 | Kneip et al. |
| 2009/0012450 | A1 | 1/2009 | Shah et al. |
| 2009/0012452 | A1 | 1/2009 | Slepicka et al. |
| 2009/0012457 | A1 | 1/2009 | Childers et al. |
| 2009/0101550 | A1 | 4/2009 | Muller et al. |
| 2009/0211975 | A1 | 8/2009 | Brugger et al. |
| 2009/0230043 | A1 | 9/2009 | Heyes et al. |
| 2010/0043694 | A1 | 2/2010 | Patel |
| 2010/0045471 | A1 | 2/2010 | Meyers |
| 2010/0089807 | A1 | 4/2010 | Heyes et al. |
| 2010/0139254 | A1 | 6/2010 | Sebestyen et al. |
| 2010/0263687 | A1 | 10/2010 | Braun et al. |
| 2011/0009797 | A1 | 1/2011 | Kelly et al. |
| 2011/0034850 | A1 | 2/2011 | Jonsson |
| 2011/0132838 | A1 | 6/2011 | Curtis et al. |
| 2011/0168614 | A1 | 7/2011 | Pouchoulin et al. |
| 2012/0164022 | A1 | 6/2012 | Muginstein et al. |
| 2012/0269907 | A1 | 10/2012 | Coates |
| 2012/0273354 | A1 | 11/2012 | Orhan et al. |
| 2012/0276549 | A1 | 11/2012 | Cunningham et al. |
| 2012/0292237 | A1 | 11/2012 | Heyes et al. |
| 2012/0308431 | A1 | 12/2012 | Kotsos et al. |
| 2013/0037465 | A1 | 2/2013 | Heyes et al. |
| 2013/0056419 | A1 | 3/2013 | Curtis |
| 2013/0092361 | A1 | 4/2013 | Wrazel et al. |
| 2013/0153495 | A1 | 6/2013 | Kelly et al. |
| 2013/0199998 | A1 | 8/2013 | Kelly et al. |
| 2013/0213891 | A1* | 8/2013 | Karoor ..... A61M 1/287 210/182 |
| 2013/0274642 | A1 | 10/2013 | Soykan et al. |
| 2014/0224736 | A1 | 8/2014 | Heide |
| 2014/0251885 | A1 | 9/2014 | Heyes |
| 2014/0271106 | A1 | 9/2014 | Alessandro et al. |
| 2014/0299544 | A1 | 10/2014 | Wilt et al. |
| 2015/0027951 | A1 | 1/2015 | Wallace et al. |
| 2015/0076053 | A1 | 3/2015 | Higgitt et al. |
| 2015/0112119 | A1 | 4/2015 | Buckberry |
| 2015/0129481 | A1 | 5/2015 | Higgitt et al. |
| 2015/0238673 | A1 | 8/2015 | Gerber et al. |
| 2015/0258263 | A1 | 9/2015 | Hogard |
| 2015/0352269 | A1 | 12/2015 | Gerber et al. |
| 2015/0359954 | A1 | 12/2015 | Gerber et al. |
| 2016/0045656 | A1 | 2/2016 | Buckberry |
| 2016/0051743 | A1 | 2/2016 | Buckberry |
| 2016/0058933 | A1 | 3/2016 | Ballantyne et al. |
| 2016/0076535 | A1 | 3/2016 | Clifton et al. |
| 2016/0077644 | A1 | 3/2016 | Ritter et al. |
| 2017/0056576 | A1 | 3/2017 | Doyle et al. |
| 2017/0167983 | A1 | 6/2017 | Klomp et al. |
| 2017/0252498 | A1 | 9/2017 | Heyes et al. |
| 2017/0296730 | A1 | 10/2017 | Soto et al. |
| 2018/0133391 | A1 | 5/2018 | Heyes et al. |
| 2018/0154059 | A1 | 6/2018 | Heyes et al. |
| 2018/0193545 | A1 | 7/2018 | Crnkovich et al. |
| 2018/0344915 | A1 | 12/2018 | Wallace |
| 2019/0001042 | A1 | 1/2019 | Buckberry |
| 2019/0015577 | A1 | 1/2019 | Garrido et al. |
| 2019/0024654 | A1 | 1/2019 | May et al. |
| 2019/0358381 | A1 | 11/2019 | Westenbrink |
| 2019/0374698 | A1 | 12/2019 | Buckberry et al. |
| 2019/0376504 | A1 | 12/2019 | Westenbrink |
| 2019/0385434 | A1 | 12/2019 | Yuds et al. |
| 2020/0030515 | A1 | 1/2020 | Merchant |
| 2020/0075159 | A1 | 3/2020 | Bardorz et al. |
| 2020/0268958 | A1 | 8/2020 | Heyes et al. |
| 2020/0276372 | A1 | 9/2020 | Milad et al. |
| 2020/0330671 | A1 | 10/2020 | Buckberry et al. |
| 2021/0110920 | A1 | 4/2021 | Heyes et al. |
| 2022/0001087 | A1 | 1/2022 | Heyes et al. |
| 2022/0160943 | A9 | 5/2022 | Buckberry et al. |
| 2022/0241480 | A1 | 8/2022 | Fincham |
| 2022/0241573 | A1 | 8/2022 | Fincham |

FOREIGN PATENT DOCUMENTS

| | | | |
|---|---|---|---|
| EM | 004375764-0001 | | 10/2017 |
| EM | 004375764-0002 | | 10/2017 |
| EM | 007955125-0002 | | 6/2020 |
| EP | 0165751 | A2 | 12/1985 |
| EP | 0754468 | A2 | 1/1997 |
| EP | 1 982 737 | A1 | 10/2008 |
| EP | 2219703 | A1 | 8/2010 |
| EP | 2955512 | A1 | 12/2015 |
| FR | 2 310 136 | | 12/1976 |
| GB | 9007955125-0001 | | 5/2020 |
| GB | 9007955125-0002 | | 5/2020 |
| JP | H04266740 | | 9/1992 |
| JP | H06261872 | | 9/1994 |
| JP | H07174659 | | 7/1995 |
| JP | 2000/130334 | | 5/2000 |
| JP | D1645323 | | 11/2020 |
| WO | WO 81/01800 | | 7/1981 |
| WO | WO 91/00113 | | 1/1991 |
| WO | WO 91/16542 | | 10/1991 |
| WO | WO 95/06205 | | 3/1995 |
| WO | WO 95/25893 | | 9/1995 |
| WO | WO 96/25214 | | 8/1996 |
| WO | WO 97/10013 | | 3/1997 |
| WO | WO 97/28368 | | 8/1997 |
| WO | WO 99/29356 | | 6/1999 |
| WO | WO 2000/006217 | | 2/2000 |
| WO | WO 00/57935 | | 10/2000 |
| WO | WO 02/066833 | | 8/2002 |
| WO | WO 02/081917 | | 10/2002 |
| WO | WO 2003/101510 | | 12/2003 |
| WO | WO 2005/044339 | | 5/2005 |
| WO | WO 2005/044339 | A2 | 5/2005 |
| WO | WO 2005/080794 | | 9/2005 |
| WO | WO 2006/120415 | | 11/2006 |
| WO | WO 2006/120417 | | 11/2006 |
| WO | WO 2008/100671 | | 8/2008 |
| WO | WO 2008/106191 | | 9/2008 |
| WO | WO 2008/135245 | | 11/2008 |
| WO | WO 2009/006489 | | 1/2009 |
| WO | WO 2009/006489 | A2 | 1/2009 |
| WO | WO 2009/024333 | | 2/2009 |
| WO | WO 2009/038834 | | 3/2009 |

(56) References Cited

FOREIGN PATENT DOCUMENTS

| | | | |
|---|---|---|---|
| WO | WO 2009/061608 | | 5/2009 |
| WO | WO 2009/127624 | | 10/2009 |
| WO | WO 2010/089130 | | 8/2010 |
| WO | WO 2010/146343 | | 12/2010 |
| WO | WO 2011/027118 | | 3/2011 |
| WO | WO 2011/068885 | | 6/2011 |
| WO | WO 2011/068885 | A1 | 6/2011 |
| WO | WO 2011/105697 | | 9/2011 |
| WO | WO 2011/105697 | A2 | 9/2011 |
| WO | WO 2011/105698 | | 9/2011 |
| WO | WO 2011/105698 | A2 | 9/2011 |
| WO | WO 2013/052680 | | 4/2013 |
| WO | WO 2013/052680 | A2 | 4/2013 |
| WO | WO 2013/057109 | | 4/2013 |
| WO | WO 2013/110906 | | 8/2013 |
| WO | WO 2013/110919 | | 8/2013 |
| WO | WO 2013/114063 | | 8/2013 |
| WO | WO 2013/114063 | A1 | 8/2013 |
| WO | WO 2013/121162 | | 8/2013 |
| WO | WO 2013/121163 | | 8/2013 |
| WO | WO 2014/072195 | | 5/2014 |
| WO | WO 2014/082855 | | 6/2014 |
| WO | WO 2014/155121 | | 10/2014 |
| WO | WO 2015/007596 | | 1/2015 |
| WO | WO 2015/022537 | | 2/2015 |
| WO | WO 2016/016870 | | 2/2016 |
| WO | WO 2017/137723 | | 8/2017 |
| WO | WO 2018/115816 | | 6/2018 |

OTHER PUBLICATIONS

He et al., "A Fluorescent Sensor with High Selectivity and Sensitivity for Potassium in Water," Journal of the American Chemical Society 2003 125 (6), 1468-1469.

Home Dialysis Tescon Aqua Tech, Aug. 1, 2020, youtube.com [online], [site visited Jan. 9, 2022], Available from internet, URL: <https://www.youtube.com/watch?v=WLLPZoS_mz4> (Year: 2020).

Kivi, Air Embolism, Healthline, Aug. 20, 2012, p. 1-5.

LHO2028 Portable Hemodialysis Machine, date unknown, aliexpress.com [online], [site visited Jan. 4, 2022], Available from internet: <https ://www.aliexpress.com/item/1005003324875329.html?randl_currency=USD&_randl_shipto=US&src=google&afffcid=1003bab3b8db4e93b9ba88522a14cfc1-1641319351626-05232-UneMJZVf&aff_fsk=UneMJZVf&aff_platform=aaf&sk=UneMJZVf&aff_trace_key= (Year: 2022).

Medical Hemodialysis Machine, date unknown, aliexpress.com [online], [site visited Jan. 4, 2022], Available from internet: <https://www.aliexpress.com/item/1005003445721549.html?_randl_currency=USD&_randl_shipto=US&src=google&aff_fcid=a524f3f9cd9b4976b6b47962f3439d62-1641319166409-02691-UneMJZVf&aff_fsk=UneMJZVf&aff_platform=aaf&sk=UneMJZVf&aff_trace_key=a524f3f9cd9b4976b6b47962f3439d62-1641319166409-02691-UneMJZVf&terminal_id=d0c2cca4b7664d128cb4801 a9ef03ff2> (Year: 2022).

Millenium HX Portable Dialysis Water System, Jul. 2, 2014, youtube.com [online], [site visited Jan. 10, 2022], Available from internet, URL: <https://www.youtube.com/watch?v=IGEbPi2CDsw> (Year: 2014).

Portable home dialysis device, Nov. 2, 2017, med-technews.com [online], [site visited Jan. 4, 2022], Available from internet: <https://www.med-technews.com/news/portable-home-dialysis-device-to-launch-next-year/ (Year: 2017).

Lee et al., "Evaluation of a New Method for Pulse Push/Pull Hemodialysis: Comparison with Conventional Hemodialysis," *ASAIO Journal* 2012, pp. 232-237.

Kyungsoo Lee, "Pulse Push/Pull Hemodialysis: Convective Renal Replacement Therapy," *Progress in Hemodialysis—From Emergent Biotechnology to Clinical Practice*, Chap. 6, pp. 113-142 (Intech 2011).

Kyungsoo Lee , "Push/Pull Based Renal Replacement Treatments," *Hemodialysis*, Chap. 22, pp. 455-474 (Intech 2013).

Jan. 5, 2015 ISR for PCT/GB2014/052486.

Feb. 16, 2016 International Preliminary Report on Patentability for PCT/GB2014/052486.

* cited by examiner

DUAL HAEMODIALYSIS AND HAEMODIAFILTRATION BLOOD TREATMENT DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present application is a *reissue patent application of U.S. Pat. No. 10,314,959, which issued 11 Jun. 2019, from U.S. patent application Ser. No. 14/911,846, filed 12 Feb. 2016, which is a* 35 USC § 371 submission of international application no. PCT/GB2014/052486, filed on 13 Aug. 2014 and published in the English language on 19 Feb. 2015 with publication no. WO 2015/022537 A1, which claims the benefit of the filing date of application no. GB 1314512.3, filed 14 Aug. 2013, the disclosures of which are incorporated by reference.

FIELD OF INVENTION

The invention relates to a blood treatment device capable of performing both hemodialysis and hemodiafiltration and methods of operating the device making it suitable for use in both types of treatment.

BACKGROUND TO THE INVENTION

Patients suffering from kidney disorders rely on a variety of external blood treatments to remove the harmful waste substances that build up in their blood over time. One of the most common methods of treatment is hemodialysis.

Hemodialysis typically involves two networks of fluid passageways [miming] *running* adjacent to one another in a counter current flow arrangement. Blood is passed through one set of tubules and a cleaning solution is passed through the other. The pH and osmotic potential of the cleaning solution is adapted such that waste compounds built up in the blood diffuse from the blood into the cleaning solution via a semi permeable membrane which separates the blood and cleaning solution sides of the network of fluid passageways.

This provides a method of gradually removing waste materials from the blood minimising fatigue to the patient. However, there are some disadvantages associated with hemodialysis not present with other forms of blood treatment.

Many mid-size and large-size waste solutes dissolved in the blood (including such as proteins and polypeptides) are difficult to remove completely from the blood using diffusion alone and it can take a long time to reduce the levels of these substances in the blood to acceptable levels. An alternative approach is to use hemodiafiltration.

Hemodiafiltration involves administering sterile cleaning solution to the blood either by employing a large hydrostatic potential to force sterile cleaning solution across a semi permeable membrane into the blood or by directly adding it to the blood; and then pulling the sterile cleaning solution, complete with dissolved waste products, back across the semi permeable membrane for subsequent disposal.

Examples of hemodiafiltration machines are disclosed in, for example "Lee, K., et al., Evaluation of a New Method for Pulse Push/Pull Hemodialysis: Comparison with Conventional Hemodialysis, ASAIO Journal, 2012, page 232-237".

This type of blood treatment is not limited by diffusion as sterile cleaning solution is allowed to mix directly with the blood. However, the rapid extraction of waste products from a patient's blood regularly leaves patients fatigued.

Accordingly, what is required is a device which is able to facilitate both methods of blood treatment during the same treatment session based on the patients specific requirements.

SUMMARY OF THE INVENTION

In a first aspect of the invention, there is provided a blood treatment device comprising: a dialyzer; a first pump for delivering a volume of cleaning solution from a cleaning solution source to the dialyzer; a second pump for removing a volume of cleaning solution from the dialyzer and delivering said cleaning solution to a drain; a first dialyzer inlet valve arranged between the first pump and an inlet of the dialyzer; a first dialyzer outlet valve arranged between an outlet of the dialyzer outlet and the second pump; each of the valves and the pumps being independently operable; and a control system configured to operate the valves and pumps in at least one first mode permitting hemodialysis and at least one second mode permitting hemodiafiltration.

The inventors have found that by using an arrangement according to the first aspect of the invention, it is possible to operate the pumps and valves to allow cleaning solution to be forced across and back through the membrane of the dialyzer to the blood as well as operate the pumps and valves to pump cleaning solution through the dialyzer in a conventional manner to permit diffusion from the blood into the cleaning solution across the semi permeable membrane down a concentration gradient. This allows for one apparatus to serve a dual purpose and means that a mix of both hemodialysis and hemodiafiltration treatments can be provided to a patient during a single session. This allows the treatment to be tailored to minimise the duration of dialysis whilst managing the fatigue levels of the patient.

The term "configured to" with reference to the control system of the invention is intended to mean that the control system is either programmed or physically arranged to operate the valves and pumps in a specific manner. The control system is programmable or configurable to operate the pumps and valves in a specific manner. The control system may be a microprocessor programmed to control the operation of the pumps and valves to effect the hemodialysis or hemodiafiltration.

Alternatively, the control system may be a mechanical arrangement which actuates the pumps and valves in a particular way to effect hemodialysis or hemodiafiltration.

In either case, switching between modes of operation may be automatic or may be effected manually.

Where the control system is a microprocessor, the control system may be adapted and/or configured to receive data corresponding to levels of waste components in the blood and, based on the data, moderate the amount of hemodialysis and hemodiafiltration of the blood treatment procedure accordingly.

Typically, the pumps used in the invention are positive displacement pumps, using pumping systems with an "in stroke" for taking in a solution to be pumped and an "out stroke" for expelling the solution out again is useful to maintain flow balance.

Preferably, the positive displacement pumps are membrane pumps. The membrane pumps typically comprise a chamber which is adapted to hold a volume of solution and a membrane sealing the chamber. The membrane can be forced down into the chamber to expel the solution from the chamber. The membrane is often a flexible membrane and is typically fabricated from an elastic material. The elastic material is often made from a plastic or polymeric material and typically forms a film sealing one end of the chamber. The membrane may extend substantially over all the chambers used in the device or each membrane pump may comprise a separate membrane in communication with the chambers.

Preferably, the pumps are arranged to pump a predetermined volume of cleaning solution. Typically the pumps used in the invention are adapted to pump the same volume of solution. Where the pumps are positive displacement pumps, the pumps are adapted to pump the same volume of solution in each single stroke. This ensures that the amount of solution pumped into the dialyzer by the first pump is the same as the amount of solution drawn from the dialyzer by the second pump.

In a further embodiment, the device may comprise one or more sensors arranged to monitor the blood pressure of the user, said sensors being in communication with the control means and wherein the control means may be additionally configured to modify the pressure of the cleaning solution generated by the pumps based on the blood pressure of the user.

This allows for fluctuations in the patient's blood pressure to be accounted for to ensure substantially constant volumetric pumping.

Keeping cleaning solution pressure and blood pressure balanced ensures consistent valve closure using the membrane and helps maintain a constant rate of blood treatment.

The dialyzer used in the invention may be a separate dialyzer device to which the machine and/or cartridge is attached or alternatively, the dialyzer may be formed on the cartridge.

The device may comprise a first cleaning solution source valve arranged between the cleaning solution source and the first pump. This ensures that when the first pump is operated to pump cleaning solution into the dialyzer no cleaning solution is able to return back towards the cleaning solution source. The device may comprise a first drain valve arranged between the second pump and the drain. This prevents the spent cleaning solution from being drawn back from the drain when the second pump is operated. The cleaning solution used in the invention is typically dialysate. The dialysate solution may be passed through one or more sterilisation means. The sterilisation means may be present in the machine. As the cleaning solution is made to enter the blood, the solution must be substantially free of pathogens.

Typically, the first pump and second pump are both operable to deliver a volume of cleaning solution from a cleaning solution source to the dialyzer and remove a volume of cleaning solution from the dialyzer, deliver said cleaning solution to a drain. Adapting both pumps to function in this way allows the roles of each pump to be periodically swapped. This is usually done at regular intervals in order to negate any small manufacturing discrepancies in the volume of the pump chambers.

The device may further comprise a second dialyzer inlet valve arranged between the second pump and the inlet of the dialyzer and a second dialyzer outlet valve arranged between the outlet of the dialyzer and the first pump. The device preferably comprises a second cleaning solution source valve arranged between the cleaning solution source and the second pump. The device may comprise a second drain valve arranged between the first pump and the drain. These valves ensure that no cleaning solution is pumped in the wrong direction.

The control system is preferably configured, in use, to alternate the operation of the valves and pumps between the at least one first mode and the at least one second mode. The valves and pumps may be independently operable to perform a mixture of blood treatment operations in a single blood treatment session.

In a preferred embodiment, the control system is configured to alternate the pump responsible for delivering cleaning solution to the dialyzer and the pump responsible for removing spent cleaning solution from the dialyzer after a given number of pumping cycles. The first pump may initially operate as the pump responsible for delivering cleaning solution to the dialyzer and the second pump may be responsible for removing spent cleaning solution from the dialyzer. As both the first and second pumps may be connected to the drain and cleaning solution source, these roles can be switched in order to accommodate minor discrepancies in the volumes of the pump chambers.

Typically, the number of pumping cycles may be two or more pumping cycles. The term "pumping cycle" is intended to refer to the sequence of operations required to pump one pump's volume of cleaning solution from the cleaning solution source and into the drain.

The pumps and valves may be formed on a disposable cartridge. Typically the cleaning solution source, pumps, valves and fluid passageways are all contained on the cartridge.

In a second aspect of the invention, there is provided a method of operating a device according to the first aspect of the invention, wherein the valves and pumps are operated in the at least one first mode permitting hemodialysis and the at least one second mode permitting hemodiafiltration.

The valves and pumps may be operated to alternate between the at least one first mode permitting hemodialysis and the at least one second mode permitting hemodiafiltration. Having a single device capable of operating in two modes to facilitate two methods of blood treatment provides a more versatile device removing the requirement to have two machines adapted to do different tasks. Further, switching between two different methods of blood treatment during a treatment session improves the process of cleaning a patient's blood.

Alternatively, there is provided a method of operating the device according to the first aspect of the invention, wherein the valves and pumps are operated in the at least one second mode permitting hemodiafiltration. Making use of an arrangement comprising two pumps allows for a method of operating a blood treatment device that allows hemodiafiltration to be performed in a pump cycle comprising only two stages. This increases the rate of flow of cleaning solution that can be passed through the dialyzer membrane allowing for faster hemodiafiltration compared to existing devices.

Typically, the at least one first mode comprises the steps of: a) operating the first pump to draw the cleaning solution from a cleaning solution source into the first pump and operating the second pump to expel spent cleaning solution from the second pump into the drain; and b) operating the first pump to expel the cleaning solution from a first pump into the dialyzer and operating the second pump to draw spent cleaning solution from the dialyzer into the second pump.

In this mode of operation, cleaning solution is passed from the first pump and into the second pump through the dialyzer allowing waste product from the blood to enter the cleaning solution via diffusion across the semi permeable membrane in the dialyzer. The cleaning solution does not pass substantially across the dialyzer membrane as it is preferentially drawn into the second pump as a result of the generated negative pressure.

The first mode may comprise the steps of: a) closing the first dialyzer inlet valve, closing the first dialyzer outlet valve, operating the first pump to draw the volume of cleaning solution from a cleaning solution source into the first pump and operating the second pump to expel the volume of cleaning solution from the second pump into the drain; and b) opening the first dialyzer inlet valve, opening the first dialyzer outlet valve, operating the first pump to expel the volume of cleaning solution from the first pump into the dialyzer and operating the second pump to draw the volume of cleaning solution from the dialyzer into the second pump.

The first mode preferably comprises the steps of: a) closing the first dialyzer inlet valve, closing the first dialyzer outlet valve, opening the first clean solution source valve, opening the first drain valve, operating the first pump to draw the volume of cleaning solution from a cleaning solution source into the first pump and operating the second pump to expel the volume of cleaning solution from the second pump into the drain; and b) opening the first dialyzer inlet valve, opening the first dialyzer outlet valve, closing the first clean solution source valve, closing the first drain valve, operating the first pump to expel the volume of cleaning solution from the first pump into the dialyzer and operating the second pump to draw the volume of cleaning solution from the dialyzer into the second pump.

The first mode may comprise the steps of: a) closing the first and second dialyzer inlet valve, closing the first and second dialyzer outlet valve, opening the first cleaning solution source valve, opening the first drain valve, closing the second cleaning solution source valve, closing the second drain valve, operating the first pump to draw the volume of cleaning solution from a cleaning solution source into the first pump and operating the second pump to expel the volume of cleaning solution from the second pump into the drain; b) opening the first dialyzer inlet valve, opening the first dialyzer outlet valve, closing the first clean solution source valve, closing the first drain valve, operating the first pump to expel the volume of cleaning solution from the first pump into the dialyzer and operating the second pump to draw the volume of cleaning solution from the dialyzer into the second pump; c) closing the first dialyzer inlet valve, closing the first dialyzer outlet valve, opening the first drain valve, operating the second pump to expel the volume of cleaning solution from the second pump into the drain; and d) closing the first drain valve, opening the second cleaning solution source valve, operating the second pump to draw the volume of cleaning solution from the clean solution source; e) opening the second dialyzer inlet valve, opening the second dialyzer outlet valve, closing the second cleaning solution source valve, operating the second pump to expel the volume of cleaning solution from the second pump into the dialyzer and operating the first pump to draw the volume of cleaning solution from the dialyzer into the first pump; f) closing the second dialyzer outlet valve, opening the second drain valve, closing the second dialyzer inlet valve, opening the second cleaning solution source valve, operating the second pump to draw the volume of cleaning solution from the cleaning solution source and operating the first pump to expel the volume of cleaning solution from the first pump into the drain.

Operating the device in a first mode as described above by swapping the roles of the first and second pumps removes error in the volume of liquid pumped due to inherent, small differences in the first and second pumps resulting from their manufacture.

Usually, the first mode comprises a pumping cycle as described above further comprising an additional step between steps b) and c), wherein the additional step comprises repeating steps a) and b) one or more times.

It may be the case that the first mode comprises a pumping cycle comprising an additional step after step f), the additional step comprising repeating steps e) and f) one or more times.

Typically, the at least one second mode comprises the steps of: a) operating the first pump to draw the volume of cleaning solution from a cleaning solution source into the first pump and operating the second pump to draw a volume of cleaning solution from the dialyzer into the second pump; and b) operating the first pump to expel the volume of cleaning solution from the first pump into the dialyzer and operating the second pump to expel the volume of cleaning solution from the second pump into the drain.

In use, these steps may be repeated continuously throughout the duration of a treatment session.

Operating the pumps and valves in this manner forces cleaning solution across the dialyzer membrane and into the blood with the first step and pulls the cleaning solution back across the dialyzer in the second step thereby effecting hemodiafiltration in a two step pumping cycle.

Typically, the second mode may comprise a pumping cycle comprising the steps of: a) closing the first dialyzer inlet valve, opening the first dialyzer outlet valve, operating the first pump to draw the volume of cleaning solution from a cleaning solution source into the first pump and operating the second pump to draw the volume of cleaning solution from the dialyzer into the second pump; and b) opening the first dialyzer inlet valve, closing the first dialyzer outlet valve, operating the first pump to expel the volume of cleaning solution from the first pump into the dialyzer and operating the second pump to expel the volume of cleaning solution from the second pump into the drain.

Even more typically, the second mode may comprise a pumping cycle comprising the steps of: a) closing the first dialyzer inlet valve, opening the first dialyzer outlet valve, opening the first cleaning solution source valve, closing the first drain valve, operating the first pump to draw the volume of cleaning solution from a cleaning solution source into the first pump and operating the second pump to draw the volume of cleaning solution from the dialyzer into the second pump; and b) opening the first dialyzer inlet valve, closing the first dialyzer outlet valve, closing the first cleaning solution source valve, opening the first drain valve, operating the first pump to expel the volume of cleaning solution from the first pump into the dialyzer and operating the second pump to expel the volume of cleaning solution from the second pump into the drain.

Usually, the second mode may comprise a pumping cycle comprising the steps of: a) closing the first and second dialyzer inlet valve, opening the first dialyzer outlet valve, closing the second dialyzer outlet valve, opening the first cleaning solution source valve, closing the second cleaning solution source valve, closing the first and second drain valves, operating the first pump to draw the volume of cleaning solution from a cleaning solution source into the first pump and operating the second pump to draw the volume of cleaning solution from the dialyzer into the second pump; b) opening the first dialyzer inlet valve, closing the first dialyzer outlet valve, closing the first cleaning solution source valve, opening the first drain valve, operating the first pump to expel the volume of cleaning solution from the first pump into the dialyzer and operating the second pump to expel the volume of cleaning solution from the second pump into the drain; c) closing the first dialyzer inlet valve, opening the second dialyzer outlet valve, opening the second cleaning solution source valve, closing the first drain valve, operating the second pump to draw the volume of cleaning solution from a cleaning solution source into the second pump and operating the first pump to draw the volume of cleaning solution from the dialyzer into the first pump; and d) opening the second dialyzer inlet valve, closing the first and second dialyzer outlet valves, closing the first cleaning solution source valve, opening the second drain valve, operating the first pump to expel the volume of cleaning solution from the first pump into the drain and operating the second pump to expel the volume of cleaning solution from the second pump into the dialyzer.

Operating the device in the second mode as described above by swapping the roles of the first and second pumps, removes error in the volume of liquid pumped due to inherent, small differences in the first and second pumps resulting from their manufacture.

In addition, by incorporating hemodiafiltration steps into a hemodialysis treatment session, proteins and other large molecules built up on the dialyzer membrane can be dislodged and/or dissolved by periodically incorporating a hemodiafiltration operation into an otherwise purely hemodialysis operating method. This ensures the sieving coefficient of the membrane can be maintained at an optimum level thereby ensuring the dialyzer membrane does not become "clogged".

Typically, the method further comprises an additional step between steps b) and c), wherein the additional step comprises repeating steps a) and b) one or more times. Even more typically, the method comprises an additional step after step d), wherein the additional step comprises repeating steps c) and d) one or more times.

In an alternative embodiment, the device can be configured wherein the second mode comprises the steps of: a) closing the first dialyzer inlet valve, opening the first dialyzer outlet valve, operating the second pump to draw the volume of cleaning solution from the dialyzer into the second pump; b) closing the first dialyzer outlet valve, operating the first pump to draw the volume of cleaning solution from the cleaning solution source into the first pump and operating the second pump to expel the volume of cleaning solution from the second pump into the drain; and c) opening the first dialyzer inlet valve, operating the first pump to expel the volume of cleaning solution from the first pump into the dialyzer.

Further, by operating the second mode in this manner there is no requirement for the sensors to be used to monitor the quantity of cleaning solution entering the patient as this can be accurately determine by counting the number of pump cycles. Further, operating the device in this way is particularly useful as a supplementary treatment technique to hemodialysis. The transfer of cleaning solution across the membrane improves dissolution of larger waste molecules which do not pass through the membrane easily during pure hemodialysis. These molecules can be removed more easily as this cleaning solution in the blood is pulled back across the dialyzer membrane and delivered to the drain. The ratio of hemodiafiltration to hemodialysis used in a single treatment is typically in the range of 5% to 95% hemodiafiltration, 10% to 85% hemodiafiltration, 20% to 80% hemodiafiltration and is most typically between 25% to 75% hemodiafiltration.

Although the amount of hemodiafiltration can be varied to suit a particular patient's requirements, it is usually the case that in a typical treatment session, the amount of cleaning solution that passes across the dialyzer membrane via diafiltration is in the range of 15 to 35 liters, or more typically in the range of 20 to 30 liters.

In another alternative embodiment, the second mode may comprise the steps of: a) closing the first dialyzer inlet valve, opening the first dialyzer outlet valve, closing the first drain valve, operating the second pump to draw the volume of cleaning solution from the dialyzer into the second pump; b) closing the first dialyzer outlet valve, opening the first cleaning solution source valve, opening the first drain valve, operating the first pump to draw the volume of cleaning solution from the cleaning solution source into the first pump and operating the second pump to expel the volume of cleaning solution from the second pump into the drain; and c) opening the first dialyzer inlet valve, closing the first cleaning solution source valve, operating the first pump to expel the volume of cleaning solution from the first pump into the dialyzer.

Preferably, the second mode comprises the steps of: a) opening the first cleaning solution source valve, operating the first pump to draw the volume of cleaning solution from the cleaning solution source into the first pump and operating the second pump to expel the volume of cleaning solution from the second pump into the drain; b) opening the first dialyzer inlet valve, operating the first pump to expel the volume of cleaning solution from the first pump into the dialyzer; and c) closing the first dialyzer inlet valve, opening the first dialyzer outlet valve, operating the second pump to draw the volume of cleaning solution from the dialyzer into the second pump.

More preferably, the second mode comprises the steps of: a) closing the first dialyzer outlet valve, opening the first cleaning solution source valve, opening the first drain valve, operating the first pump to draw the volume of cleaning solution from the cleaning solution source into the first pump and operating the second pump to expel the volume of cleaning solution from the second pump into the drain, b) opening the first dialyzer inlet valve, closing the first cleaning solution source valve, operating the first pump to expel the volume of cleaning solution from the first pump into the dialyzer; and c) closing the first dialyzer inlet valve, opening the first dialyzer outlet valve, closing the first drain valve, operating the second pump to draw the volume of cleaning solution from the dialyzer into the second pump.

The second mode may comprise the steps of: a) closing the first dialyzer outlet valve, opening the first cleaning solution source valve, opening the first drain valve, operating the first pump to draw the volume of cleaning solution from the cleaning solution source into the first pump and operating the second pump to expel the volume of cleaning solution from the second pump into the drain; b) opening the first dialyzer inlet valve, closing the first cleaning solution source valve, operating the first pump to expel the volume of cleaning solution from the first pump into the dialyzer; c) closing the first dialyzer inlet valve, opening the first dialyzer outlet valve, closing the first drain valve, operating the second pump to draw the volume of cleaning solution from the dialyzer into the second pump; d) opening the first drain valve, closing the first dialyzer outlet valve, operating the second pump to expel the cleaning solution from the second pump into the drain; e) closing the first drain valve, opening the second source valve, closing the second dialyzer inlet valve and operating the second pump to draw a volume cleaning solution from the cleaning solution source into the second pump; f) closing the second source valve, opening the second dialyzer inlet valve and operating the second pump to expel the volume of cleaning solution from the second pump into the dialyzer; g) closing the second dialyzer inlet, opening the second dialyzer outlet, closing the second drain valve and operating the first pump to draw the volume of cleaning solution into the first pump; and h) opening the second drain valve, closing the second dialyzer outlet valve, opening the second source valve and operating the first pump to expel the volume of cleaning solution from the first pump into the drain and operating the second pump to draw a volume of cleaning from the source into the second pump.

The method may comprise the step in between steps c) and d) of repeating steps a) to c) one or more times. Further, it may be the method comprises the step after step h) of repeating steps f) to h) one or more times. Usually, these steps a) to c) and steps f) to h) are repeated once.

In a still further embodiment of the invention, the second mode may comprise the steps of: a) operating both the first and second to draw a volume of cleaning solution from a cleaning solution source into the first and second pumps; b) operating both pumps to expel the volume of cleaning solution into the dialyzer and across the membrane of the dialyzer; c) operating the first and second pumps to draw a the volume of cleaning solution from the dialyzer into both pumps; and d) operating both the first and second pumps to expel the volume of cleaning solution from the pumps into the drain.

The second mode preferably comprises: a) opening both the first and second source valves and first and second dialyzer inlet valves, closing both the first and second dialyzer outlet valves and the first and second drain valves and operating the first and second pumps to draw cleaning solution from the cleaning solution source into the first and second pump chambers; b) closing the first and second source valves and the first and second dialyzer outlet valves, opening the first and second dialyzer inlet valves and operating both the first and second pumps to expel the dialysate from the first and second pump chambers into the dialyzer; c) opening the first and second dialyzer outlet valves, closing the first and second dialyzer inlet valves and operating both the first and second pumps to draw a volume cleaning solution from the dialyzer into the first and second pump chambers; d) opening the first and second drain valves, closing the first and second dialyzer outlet valves and operating both the first and second pumps to expel a volume of cleaning solution from the first and second pump chambers into the drain.

By operating both pumps to deliver cleaning solution to the dialyzer, this provides a greater volume of cleaning solution which can pass across the membrane and into the blood in a single step of the pumping cycle.

The duration of each step of the methods described herein may be in the range of 0.5 seconds to 10 seconds. The duration of each step may be in the range of 1 second to 5 seconds and it is often the case that each method step will be between 1 and 2 seconds in length.

The device of the present invention may be operated using one or more of the second modes discussed and further, it may be the case that the device uses more than one of these second modes during a single treatment session.

BRIEF DESCRIPTION OF THE DRAWINGS

The invention will now be described with reference to the following figures.

DESCRIPTION

Figure 1:
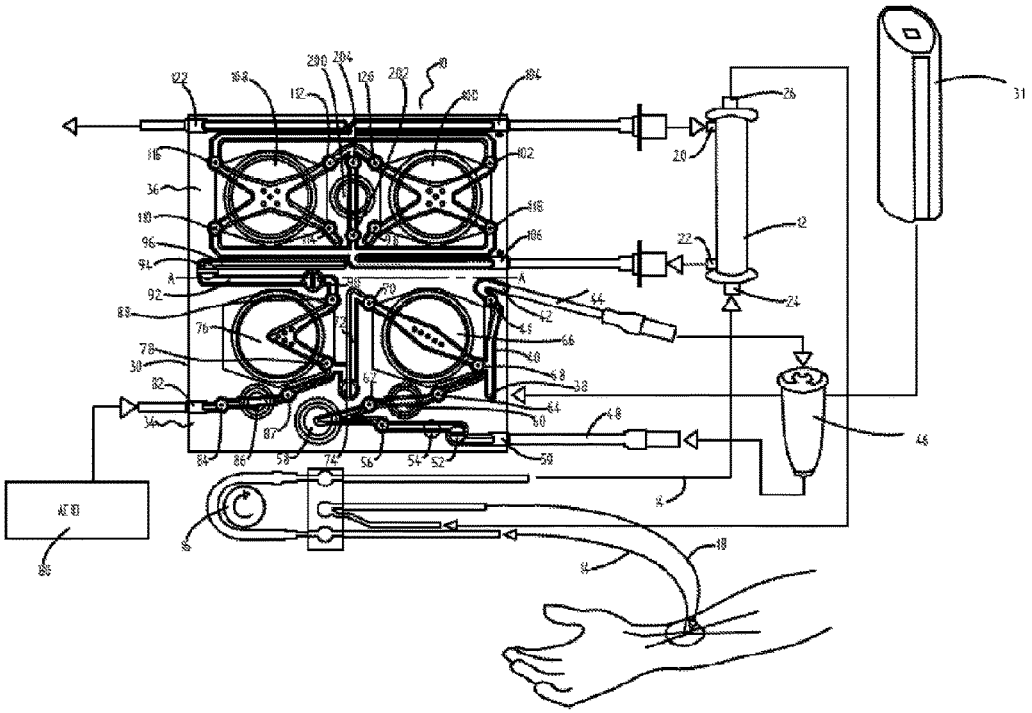
FIG. 1 shows a schematic of a dialysis system having a disposable cartridge comprising a fluid path defined by pumps and valves.
Figure 1A:
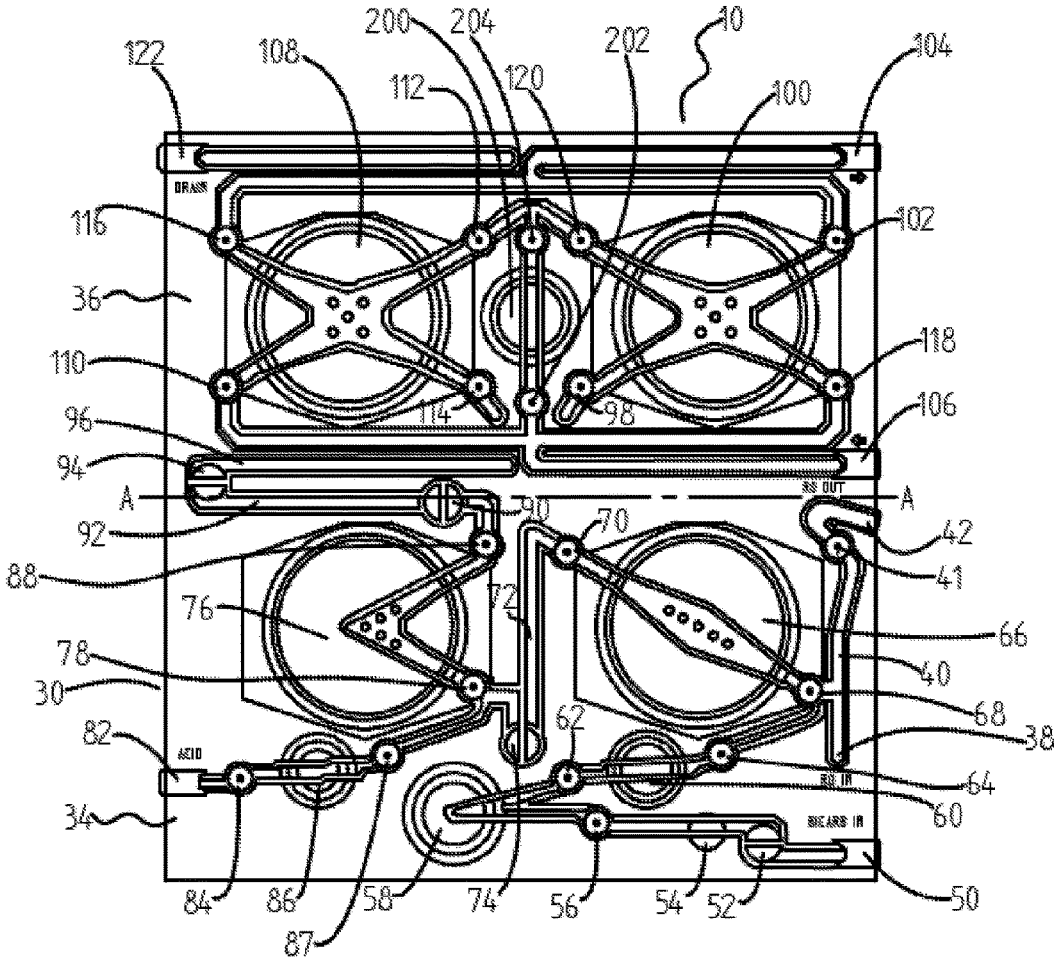
FIG. 1a shows a detailed schematic view of the cartridge of FIG. 1.

Referring to FIGS. 1 and 1a, a dialysis system, generally referred to as 10, is shown. A dialyzer 12 receives blood via an arterial line 14 connected to a patient by a vascular access device (not shown for clarity), for example a hollow needle as typically used for drawing blood from a patient. The blood is pumped from the patient to the dialyzer by a peristaltic pump 16. The blood passes through the dialyzer in a known manner and is returned to the patient via a venous line 18. The dialyzer 12 comprises a cylindrical tube closed by opposing ends. A semi-permeable membrane (not shown) is provided within the dialyzer tube and separates the patients blood from a dialysate (cleaning) solution. The membrane extends substantially between the opposing ends of the cylinder. The dialysate solution removes impurities from the patients blood in a known manner.

The dialyzer has an inlet 20 for receiving clean dialysate solution and an outlet 22 for removing spent dialysate solution from the dialyzer 12. The dialyzer also has an inlet 24 for receiving untreated blood from the peristaltic pump 16 and an outlet 26 for returning processed blood to the patient. The dialyzer 12 is typically provided in a substantially upright orientation, in use, with the patient's blood flowing longitudinally through the dialyzer 12 from the blood inlet 24 to the blood outlet 26. The dialysate solution inlet 20 and dialysate solution outlet 22 are configured to be orientated substantially orthogonal to the blood inlet 24 and blood outlet 26, and to provide a counter-flow. Dialysate solution is circulated through the hemodialysis machine at a fluid flow rate in the region of 400 ml/min for approximately four hours.

The dialysis system defines a fluid circuit including a cartridge 30 as will now be described. The cartridge 30 is a consumable component in the hemodialysis machine described.

The cartridge 30 is formed from an acrylic plastic such as SG-10 and has a machine side and a patient side. The cartridge 30 defines pump chambers which are closed by respective diaphragms, formed from, for example, DEHP-free PVC, to define respective pumps. In this embodiment, each diaphragm is part of a single, common sheet of material applied to the machine side of the cartridge 30. The individual diaphragms are operable by pneumatic pressure applied thereto.

A series of flow paths are formed in the cartridge 30 for carrying dialysate solution constituted from water, bicarbonate solution and acid solution. The flow paths are located between the sheet of material closing the machine side of the cartridge 30 and a further sheet of the same material closing the patient side of the cartridge 30.

In use, the variation of pressure applied to the flexible diaphragm of each pump chamber is controlled by conventional valving. A pressure source applies either a positive or negative pressure to one side of the diaphragm of each pump chamber, as required, to pump fluid through the fluid paths in the cartridge 30, in a circuit defined by a plurality of valves.

The valves of the cartridge 30 are conventional diaphragm valves defined by respective openings in the cartridge 30 and closed by respective flexible diaphragms. Each valve is operable by applying a negative pressure to the diaphragm to open the valve and applying a positive pressure to the diaphragm to close the valve. The diaphragm of each valve is part of the single, common sheet of material applied to the machine side of the cartridge 30. The valves are opened and closed according to a flow control strategy, as will become apparent.

The machine side of the cartridge 30 abuts a pump driver (not shown) comprising a platen having a plurality of recessed surfaces, each recessed surface substantially corresponding in geometry and volume to a pump chamber defined in the cartridge 30. Each recessed surface has a fluid port connectable with a source of positive fluid, typically, pressure and, with a source of negative fluid pressure via a valve.

The positive and negative fluid pressure sources include a pressure pump and a vacuum pump respectively. When the valve is operated to allow fluid to flow into a recessed surface from the source of positive fluid pressure, the diaphragm moves into a corresponding pump chamber and any fluid, i.e. dialysate solution, therein is expelled from that pump chamber via the series of flow paths. When the valve is operated to allow fluid to flow out of a recessed surface to the source of negative fluid pressure, the diaphragm is moved away from a pump chamber and into the corresponding recessed surface to permit fluid to be drawn into that pump chamber via the series of flow paths. The surface of the pump chambers and of the platen provide a positive stop for each diaphragm, to prevent overstretching thereof. The positive stop ensures that the volume of fluid drawn into and pumped from the pump chambers is accurately controlled.

Figure 2:
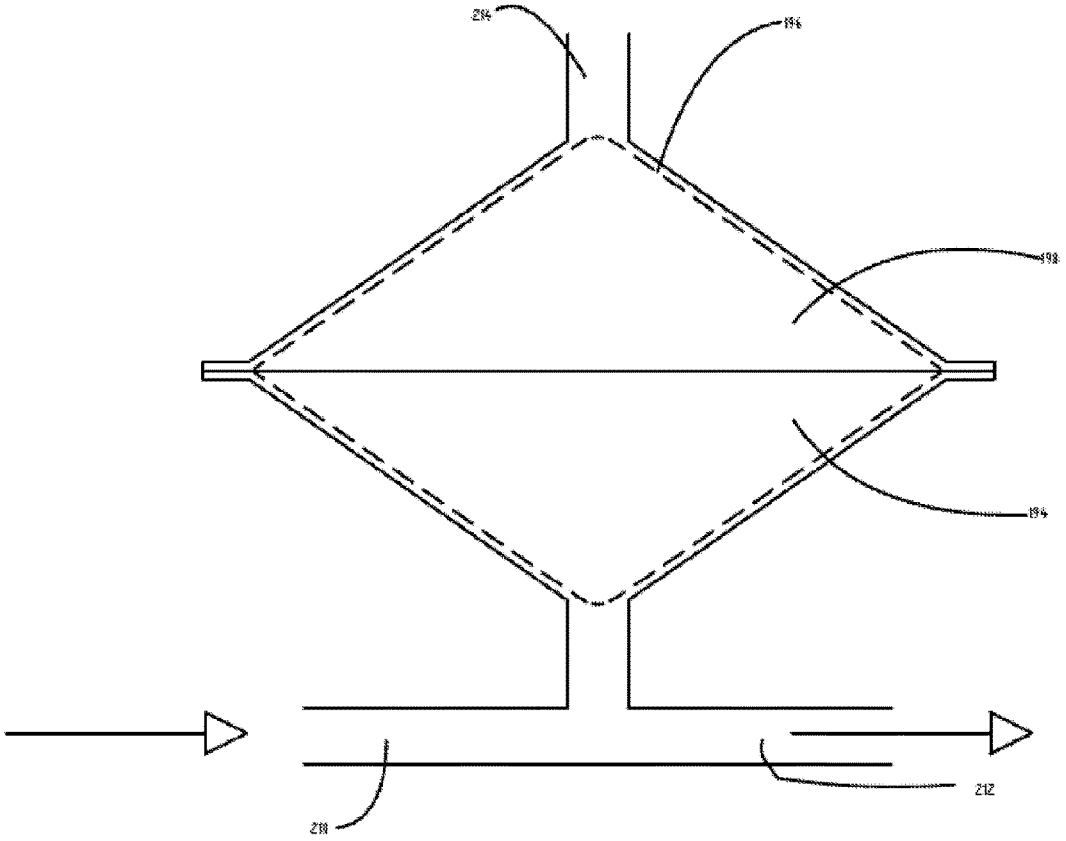
FIG. 2 shows a schematic view of the operation of a pump of the type defined by the disposable cartridge.

The cartridge 30 has two main functions, preparation of dialysate solution and flow balance. Each function is performed by a separate part of the cartridge as illustrated in FIGS. 1 and 2 by the schematic separation of the cartridge into two parts by the line A-A in the figures. The dialysate preparation function is performed by one part of the cartridge, generally referred to at 34 and the flow balance function is performed by the other part of the cartridge, generally referred to at 36. The cartridge 30 prepares an accurately mixed homogenous dialysate solution and ensures that the flow of clean dialysate supplied to the dialyzer 12 matches (to within clinical tolerances) the volume of spent dialysate drawn from the dialyzer 12.

The cartridge 30 is provided with a plurality of connections to and from the cartridge 30 as described below.

A first inlet port 38, from hereon referred to as the water inlet port, defined in the machine side of the cartridge 30 receives purified water from a purified water supply 31 such as a reverse osmosis water supply.

A first outlet port 42, from hereon referred to as the water outlet port, defined in an edge of the cartridge 30 directs the purified water to a first dialysate solution constituent which, in the illustrated embodiment shown in FIGS. 1 and 1a, is bicarbonate 46.

A second inlet port 50, from hereon referred to as the bicarbonate inlet port, defined in the same edge of the cartridge 30 as the water outlet port 42 receives purified water mixed with the bicarbonate 46.

A third inlet port 82, from hereon referred to as the acid inlet port, defined in the opposite edge of the cartridge 30 to the water outlet port 42 and bicarbonate inlet port 50 receives a second dialysate solution constituent which, in the illustrated embodiment shown in FIGS. 1 and 1a, is acid 80.

A second outlet port 104, from hereon referred to as the clean dialysate solution outlet port, is defined in the same edge of the cartridge as the water outlet port 42 and the bicarbonate inlet port 50. The clean dialysate outlet port 104 directs clean dialysate solution to the dialyzer 12.

A fourth inlet port 106, from hereon referred to as the spent dialysate solution inlet port, is defined in the same edge of the cartridge 30 as the water outlet port 42, bicarbonate inlet port 50 and clean dialysate outlet port 104. The spent dialysate solution inlet port 106 receives spent dialysate solution from the dialyzer 12.

A third outlet port 122, from hereon referred to as the drain port, is defined in the same edge of the cartridge as the acid inlet port 82. The drain port 122 directs spent dialysate solution out of the cartridge 30.

Dialysate Preparation

Dialysate solution is prepared in the cartridge 30 by combining purified water with two dialysate constituents, namely a bicarbonate solution and an acid solution.

Purified water is admitted into the cartridge 30 from a purified water supply 31 via the water inlet port 38. The purified water passes through a channel 40 via a water inlet valve 41, when open, and exits the cartridge 30 at the water outlet port 42. From here, the purified water is carried by a tube 44 through a bicarbonate cartridge 46 in a known manner to generate a purified water and bicarbonate solution. The purified water and bicarbonate solution is carried by a tube 48 and re-admitted into the cartridge 30 via the bicarbonate inlet port 50.

The temperature of the bicarbonate solution is measured at sensing port 52 and the bicarbonate solution pressure is measured at sensing port 54. The bicarbonate solution passes a bicarbonate control valve 56, when open, before entering a bicarbonate solution reservoir 58 having an inlet and an outlet. The bicarbonate control valve 56 is closed when flow therethrough is not required.

A bicarbonate dosing pump chamber 60 having an inlet and an outlet receives the bicarbonate solution from the bicarbonate solution reservoir 58 through a bicarbonate dosing pump inlet valve 62. The bicarbonate dosing pump chamber 60 is closed by a diaphragm to define a bicarbonate dosing pump which, upon actuation of the diaphragm, pumps the bicarbonate solution from the bicarbonate dosing pump 60 to a first mixing pump chamber 66 (bicarbonate pump chamber). The bicarbonate dosing pump 60 has a bicarbonate dosing pump outlet valve 64 which is closed when the bicarbonate dosing pump inlet valve 62 is open. The bicarbonate dosing pump outlet valve 64 is opened to permit bicarbonate solution to be pumped to the bicarbonate pump chamber 66. When the bicarbonate dosing pump outlet valve 64 is open, the bicarbonate dosing pump inlet valve 62 is closed to prevent bicarbonate solution from being pumped back into the bicarbonate solution reservoir 58.

The bicarbonate pump chamber 66 having an inlet and an outlet receives the purified water and bicarbonate solution from the bicarbonate dosing pump 60 via a bicarbonate pump inlet valve 68. The bicarbonate pump inlet valve 68, when open, can also admit purified water into the bicarbonate pump chamber 66 from the water inlet port 38. The bicarbonate pump chamber 66 is closed by a diaphragm to define a pump which, upon actuation of the diaphragm, pumps the bicarbonate solution and purified water therein through a bicarbonate pump outlet valve 70 to a second mixing pump chamber 76 (acid pump).

When the bicarbonate pump inlet valve 68 is open, the bicarbonate pump outlet valve 70 and water outlet valve 41 are closed. When the bicarbonate pump outlet valve 70 is open, the bicarbonate pump inlet valve 68 is closed to prevent the bicarbonate and purified water solution from being pumped back into channel 40.

From the bicarbonate pump outlet valve 70, the bicarbonate and purified water solution enters a sensor channel 72 in which the hemodialysis machine measures the conductivity of the bicarbonate and purified water solution in a known manner. The bicarbonate and purified water solution then enters a temperature sensor 74 before, if the conductivity and temperature of the bicarbonate and purified water solution are within tolerance, entering the acid pump chamber 76.

The acid pump chamber 76 having an inlet and an outlet receives the bicarbonate and purified water solution from the bicarbonate pump 66 via an acid pump inlet valve 78. The acid pump inlet valve 78, when open, can also admit an acid solution into the pump chamber 76. The acid pump chamber 76 is closed by a diaphragm to define a pump which, upon actuation of the diaphragm, pumps the acid solution, bicarbonate solution and purified water therein through an acid pump outlet valve 88 to the first flow balance pump chamber 100. When the acid pump inlet valve 78 is open, the acid pump outlet valve 88 is closed. When the acid pump outlet valve 88 is open, the acid pump inlet valve 78 is closed.

The acid solution is admitted into the cartridge 30 from a pre-determined supply of acid 80 via the acid solution inlet port 82. From the acid solution inlet port the acid solution passes through an acid dosing pump chamber 86 via an acid dosing pump inlet valve 84 and an acid dosing pump outlet valve 87. The acid dosing pump outlet valve 87 is closed when the acid dosing pump inlet valve 84 is open. The acid dosing pump inlet valve 84 is closed when the acid dosing pump outlet valve 87 is open.

The dialysate solution exits the acid pump chamber via the acid pump outlet valve 88 and passes through a first dialysate solution temperature sensor 90 and a first dialysate solution conductivity sensor 92. A second dialysate solution temperature sensor 94 and a second dialysate solution conductivity sensor 96 are provided to corroborate the data provided by the first dialysate solution temperature sensor 90 and the first dialysate solution conductivity sensor 92. Providing the data measured by sensors 90, 92, 94 and 96 is within tolerance, the dialysate solution is admitted into a first flow balance pump chamber 100

Flow Balance

The flow balance function of the cartridge 30 provides first and second flow balance pump chambers 100, 108, each having two inlets and two outlets to define two independent flow paths therethrough. The first and second flow balance pump chambers 100, 108 are of approximately equal volume. Either the first or second flow balance pump chamber 100, 108 pumps dialysate solution to a dialyzer 12 and the other of the first or second flow balance pump chambers 100, 108 pumps dialysate solution from the dialyzer 12 to the drain port 122. After every approximately 20 strokes of the first and second flow balance pumps 100, 108, their function is reversed.

From this point onwards, dialysate solution will be referred to as either clean dialysate solution or spent dialysate solution. Clean dialysate solution is intended to mean dialysate solution that is either new dialysate solution or clean dialysate solution that has been treated to remove waste product therefrom. Spent dialysate solution is intended to mean dialysate solution that has passed through the dialyzer 12 to remove waste fluids from a patient's blood into the dialysate solution.

Each of the first and second flow balance pump chambers 100, 108 are closed by a diaphragm to define respective pumps. The diaphragm is actuated away from a pump chamber by a negative pressure source to draw a volumetrically measured quantity of dialysate solution into the pump chamber. The diaphragm is actuated toward the pump chamber to pump the fluid therein out of an outlet.

The first flow balance pump chamber 100 has a clean dialysate solution inlet valve 98 for receiving clean dialysate solution from the acid pump 76 and a clean dialysate solution outlet valve 102 for pumping clean dialysate solution to the dialyzer 12. The first flow balance pump chamber 100 also has a spent dialysate solution inlet valve 118 for receiving spent dialysate from the dialyzer 12 and a spent dialysate solution outlet valve 120 for pumping the spent dialysate to drain via drain outlet port 122.

At any one time, only one of valves 98, 102, 118 or 120 will be open and the other three valves will be closed. The flow balance function, as described above, requires alternating the function of each flow balance pump approximately every 20 cycles. Therefore, when the first flow balance pump 100 is pumping clean dialysate solution to the dialyzer 12, only valves 98 and 102 are in use and when the first flow balance pump 100 is pumping spent dialysate solution from the dialyzer 12 to drain, only valves 118 and 120 will be in use.

The clean dialysate solution is pumped out of the first flow balance pump chamber 100 through the first flow balance pump clean dialysate solution outlet valve 102, upon closure of the first flow balance pump clean dialysate inlet valve 98, to the dialyzer 12 via the dialyzer outlet port 104.

Spent dialysate solution returns to the cartridge 30 from the dialyzer 12 via the dialyzer inlet port 106. The second flow balance pump chamber 108 has a spent dialysate solution inlet valve 110 for receiving spent dialysate solution from the dialyzer 12 and a spent dialysate solution outlet valve 112 for pumping the spent dialysate solution to drain via drain outlet port 122. The second flow balance pump 108 also has a clean dialysate solution inlet valve 114 for receiving clean dialysate solution from the acid pump chamber 76 and a clean dialysate solution outlet valve 116 for pumping clean dialysate solution to the dialyzer 12.

At any one time, only one of valves 110, 112, 114, 116 will be open and the other three valves will be closed. When the second flow balance pump 108 is pumping clean dialysate solution to the dialyzer 12, only valves 114 and 116 will be in use and when the second flow balance pump 108 is pumping spent dialysate solution from the dialyzer 12 to drain, only valves 114 and 116 will be in use.

In the illustrated example, the operation of the first and second flow balance pumps 100, 108 can be switched so that the first flow balance pump 100 is used to draw spent dialysate solution from the dialyzer 12 and the second flow balance pump 108 is used to pump clean dialysate solution into the dialyzer 12 as described below.

The clean dialysate solution is drawn into the second flow balance pump chamber 108 from the acid pump 76 via the second flow balance pump clean dialysate solution inlet valve 114 upon actuation of the diaphragm. The clean dialysate solution is then pumped from the second flow balance pump chamber 108 via the second flow balance pump clean dialysate solution outlet valve 116, upon closure of the clean dialysate solution inlet valve 114, to the dialyzer 12.

Spent dialysate solution from the dialyzer 12 is drawn into the first flow balance pump 100 via the second flow balance pump spent dialysate solution inlet valve 118. The spent dialysate solution is then pumped out of the first flow balance pump chamber 100 via the second flow balance pump spent dialysate solution outlet valve 120, upon closure of the spent dialysate solution inlet valve 118, to drain via drain outlet port 122.

The volume of fluid that is returned from the dialyzer 12 is greater than the volume of fluid that is pumped to the dialyzer via the first or second flow balance pump 100, 108. The first and second flow balance pumps have fixed volumes meaning that the excess fluid volume cannot be accommodated in the first or second flow balance pump. An ultrafiltration pump 200 is provided between the first and second flow balance pumps 100, 108 and has an inlet valve 210 and an outlet valve 212. The ultrafiltration pump 200 comprises a concave recess in the cartridge closed by a flexible diaphragm, the concave recess and the flexible diaphragm defining an ultrafiltration pump chamber.

In use, the inlet valve 210 of the ultrafiltration pump 200 is opened to allow the ultrafiltration pump to draw in a pre-determined volume of spent dialysate solution. When the inlet valve 210 of the ultrafiltration pump is open, the outlet valve 212 of the ultrafiltration pump 200 is closed. When the ultrafiltration pump 200 has received a volume of spent dialysate solution, the outlet valve 212 is opened and the spent dialysate solution in the ultrafiltration pump chamber is pumped through the outlet valve 212 to drain via the drain outlet port 122. When the outlet valve 212 of the ultrafiltration pump 200 is open, the inlet valve 210 of the ultrafiltration pump 200 is closed.

The purpose of the ultrafiltration pump is to remove excess fluid generated by the patient. By separating the ultrafiltration pump operation from the flow balance pumps and by employing a pump arrangement described herein, fluid can be removed from the dialyzer at appropriate intervals between the stages of the operation of the flow balance pumps, without requiring modification to the flow balance pump operation. Usually, the ultrafiltration pump will remove fluid from the dialyzer during a pump swapping operation of the flow balance pumps and this may be done in the range of once every 10 to once every 30 flow balance pump cycles. Typically, fluid is removed from the dialyzer by the ultrafiltration pump approximately once every 20 pump cycles.

FIG. 2 shows a representative view of a flow balance pump 100 according to the present invention. The flow balance pump chamber 194 is provided on the cartridge and is closed by a diaphragm 196 which, at rest, sits across the pump chamber 194. The pump chamber receives either clean or spent dialysate solution via a dialysate solution inlet port 210 and pumps dialysate solution from the pump chamber via a dialysate solution outlet port 212.

The cartridge 30 is removably mounted into a hemodialysis machine which has a flow balance pump cavity 198 substantially corresponding in dimension and shape to the pump chamber 194. Upon supply of positive or negative pressure via a pump cavity pressure inlet port 214, the diaphragm is actuated into either the pump chamber 194 or pump cavity 198 to either draw fluid into the pump chamber 194 or pump fluid from the pump chamber 194.

Cartridge Cleaning

After each use, the hemodialysis machine requires sanitising to prevent contamination of a patient's bloodstream during subsequent dialysis sittings. The removable cartridge 30, as described above, is usually disposed of after each sitting. In one embodiment of the invention, the cartridge 30 is sanitised to allow re-use in subsequent dialysis sittings.

Operation of the Device

Figure 3:
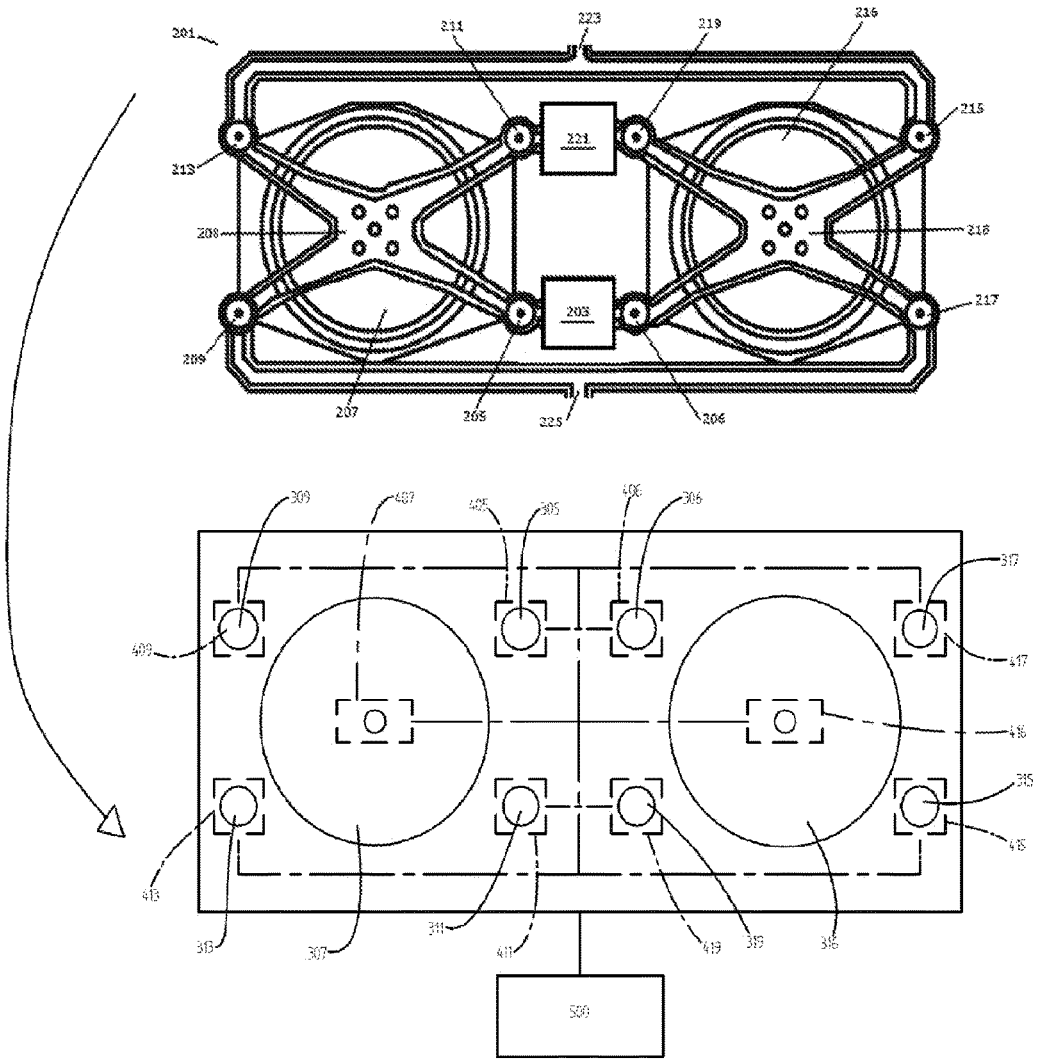
FIG. 3 shows a schematic view of the pump and valve arrangement of the invention.

FIG. 3 shows a schematic representation of the pump and valve arrangement 201 of the invention. In this case, the pump and valve arrangement 201 is provided by the combination of a membrane pump cartridge (or part cartridge) and a vacuum pump array with platen. The membrane pump cartridge is similar in layout to the flow balance pump arrangement described above.

The membrane pump cartridge comprises first and second source valves 205, 206, first and second pumps 207, 216 and first and second pump chambers 208, 218, first and second dialyzer inlet valves 209, 217 and first and second dialyzer outlet valves 213, 215.

The vacuum pump array and platen comprises a platen having a pattern of circular depressions which correspond in position and size to the valves and pumps on the pump cartridge. In the figure, these are numbered 100 higher than the membrane pump features.

Each depression has an aperture at the base thereof which is in fluid communication with an associated vacuum pump. Each vacuum pump, shown in broken lines as they sit on the rear face of the platen, is numbered 100 higher than the respective associated platen feature.

All of the vacuum pumps are connected to a control system 500. The control system 500 is a microprocessor which operates the vacuum pumps 405-419 in a manner so as to effect either hemodiafiltration or hemodialysis as described below. The connection to the pumps may be wired or wireless. Wireless connection options include IR, Bluetooth or WIFI, amongst others.

The dialysate is produced elsewhere on the cartridge by mixing acid and bicarbonate compounds with a set volume of de-ionised, water provided by a reverse osmosis machine which has been sterilised as is described above. This forms the source of dialysate 327 used by the pump and valve arrangement 201.

By selectively operating the vacuum pumps, the control system controls the opening and closure of the valves as well as actuation of the first and second pumps. The microprocessor control system is programmable to operate the valves in a variety of different configurations. Based on the programming of the controller, the controller will communicate with each of the valves or means for operating the valves, so that each valve may be opened and closed independently based on the programming entered into the controller by the user, skilled operator or programme instructions.

First Mode of Operation—Hemodialysis

The pumping cycle of the first mode of operation of the arrangement 201 begins with closure of the first and second dialyzer inlet valves 209, 217 and the first and second dialyzer outlet valves 213, 215. The first source valve 205 and the first drain valve 219 are opened, the second source valve 206 and second drain valve 211 are closed. The first pump 207 is then operated to draw dialysate 327 from the dialysate source 203 into the first pump chamber 208 of the first pump 207 and the second pump 216 is operates to expel dialysate 327 within the second pump chamber 218 of the second pump 216 into the drain 221. Accordingly, the dialysate 327 in the dialysate source 203 is drawn into the first pump chamber 208 by the negative pressure created as the membrane of the first pump chamber 208 is drawn away from the pump chamber by vacuum means in the dialysis machine (not shown). The dialysate 327 in the second pump chamber 218 is subjected to a positive pressure as the membrane in the second pump 216 is forced into the second pump chamber 218 thus driving the dialysate out through the open first drain valve 219 to be discarded.

In the next stage of the pump cycle, the first dialyzer inlet valve 209 and the first dialyzer outlet valve 215 are opened and the first source valve 205 and the first drain valve 219 are closed. The first pump 207 is then actuated to expel the dialysate 327 from within the first pump chamber 208 into the dialyzer (not shown) and the second pump 216 is actuated to pull spent dialysate 327 from the dialyzer (not shown) into the second pump chamber 218. In this step, the dialysate 327 in the first pump chamber 208 has a positive pressure applied to it as the membrane is force down into the first pump chamber 208 thereby forcing the dialysate 327 through the dialysis circuit and into the dialyzer. In the dialyzer, dialysate 327 is passed in a typically counterflow arrangement to the blood of the patient and waste products diffuse across the dialyzer membrane into the dialysate 327 via diffusion. The movement of the dialysate 327 through the dialyzer and into the second pump chamber is assisted by a negative pressure generated by the membrane of the second pump chamber which is retracted by the vacuum means on the dialysis machine, operated by the device's controller. These two stages are repeated and then, in the third stage of the pump cycle, the first dialyzer inlet valve 209 and first dialyzer outlet valve 215 are closed, the first drain valve 219 is opened and second pump 216 actuated to expel the spent dialysate 327 from the second pump chamber 218 into the drain 221. Accordingly, after the completion of this step, both pump chambers 208, 218 are empty.

In the fourth step of the cycle, the first drain valve 219 is closed and the second source valve 206 is opened in order to allow the second pump 216 to draw dialysate from the source 203 into the second pump chamber 218. In the fifth step, with the second pump chamber 218 now filled, the second dialyzer inlet valve 217 the second dialyzer outlet valves 213 are opened and the second source valve is closed. The second pump 216 is actuated to expel the dialysate in the second pump chamber 218 into the dialyzer (not shown) and the first pump 207 is actuated to draw dialysate from the dialyzer into the first pump chamber 208. This allows the same operation as was carried out in the first and second steps to proceed but with the roles of the pumps 207, 216 swapped around. Thus any small discrepancies between the volumes of the two pump chambers 208, 218 are cancelled out.

The fourth and fifth steps are repeated and finally, the second dialyzer outlet valve 213 and second dialyzer inlet valve 217 are closed, the second drain valve 211 and second source valves are opened and the first pump 207 is operated to expel the dialysate from the first pump chamber 208 into the drain 221.

Second Mode of Operation—Hemodiafiltration (Twin Pumping)

The pumping cycle of the second mode of operation of the arrangement 201 begins with opening both the first and second source valves 205, 206 and first and second dialyzer inlet valves 217, 217 together with closing both the first and second dialyzer outlet valves 213, 215 and the first and second drain valves 205, 206. The first and second pumps 207, 216 are both actuated to draw dialysate from the source 203 into the first and second pump chambers 208, 218 respectively. Accordingly, dialysate 327 drawn into both chambers 208, 218 from the dialysate source 203 due to the negative pressure created by the movement of the membrane in the pumps 207, 216.

In the second step, the first and second source valves 205, 206 and the first and second dialyzer outlet valves 213, 215 are closed, the first and second dialyzer inlet valves 209, 217 are opened and both the first and second pumps 207, 216 are actuated to expel the dialysate from the first and second pump chambers 208, 218 respectively into the dialyzer. Thus, when the pumps 207, 216 are activated a positive pressure is generated which forces dialysate 327 into the dialyzer. As the dialyzer outlet valves 213, 215 are closed, the dialysate 327 has nowhere else to go and so at least some of the dialysate 327 passes across the semipermeable membrane of the dialyzer and into the blood side of the dialyzer. This allows the dialysate 327 to mix with the blood and dissolve many of the harmful waste products built up in the blood.

In the third step, the first and second dialyzer outlet valves 213, 215 are opened, the first and second dialyzer inlet valves 209, 217 are closed and both the first and second pumps 207, 216 are actuated to draw spent dialysate from the dialyzer into the first and second pump chambers 208, 218 respectively. Because the dialysate source valves 205, 206 are closed, the negative pressure generated by the pumps 207, 216 is felt by the dialyzer and this draws the dialysate 327, along with dissolved and associated waste components, back across the semipermeable dialyzer membrane and fills the pump chambers 208, 218. As such, there is substantially no net transfer of dialysate to the patient's blood. The duration of the steps in each of the methods of the invention is typically about 1 second.

Finally, the first and second drain valves 211, 219 are opened, the first and second dialyzer outlet valves 215, 213 are closed and both the first and second pumps 207, 216 are actuated to expel spent dialysate from the first and second pump chambers 208, 218 respectively into the drain 221.

Second Mode of Operation—Hemodiafiltration (Split Pumping)

Alternatively the pumping cycle of the second mode of operation of the arrangement 201 may begin with closure of the first and second dialyzer inlet valves 209, 217 opening the first dialyzer outlet valve 215, closing the second dialyzer outlet valve 213, opening the first source valve 205, closing the second source valve 206, closing the first and second drain valves 219, 211. The first pump 207 is then actuated to draw dialysate 327 from the source 203 into the first pump chamber 208 and the second pump 216 is actuated to draw dialysate 327 from the dialyzer into the second pump chamber 218. Accordingly, dialysate 327 is drawn into both pump chambers 208, 218 by negative pressure created in both pumps 207, 216. The dialysate 327 drawn from the dialyzer is pulled from the patient's blood, across the semipermeable membrane of the dialyzer and into the second pump chamber 218. As the first dialyzer inlet valve 209 is closed, the dialysate 327 does not flow backwards along the dialysate 327 circuit into the first pump chamber 208. The first pump chamber 208 is instead filled by drawing dialysate 327 from the dialysate source 203.

In the second step, the first dialyzer inlet valve 209 and the first drain valve 219 are opened, the first dialyzer outlet valve 215 and the first source valve 205 are closed and the first pump 207 is actuated to expel dialysate from the first pump chamber 208 into the dialyzer and the second pump 216 is actuated to expel dialysate from second pump chamber 218 into the drain 221. Thus, dialysate 327 in the first pump chamber 208 is forced under positive pressure into the dialyzer but as the dialyzer outlet valves 215, 213 are closed, the dialysate has nowhere else to go except across the semipermeable membrane of the dialyzer and into the blood side of the dialyzer.

These two steps are repeated and then, in the third step, the first dialyzer inlet valve 209 and the first drain valve are closed 219, the second dialyzer outlet valve 213 and second source valve 206 are opened. The second pump 216 is actuated to draw dialysate from the source into the second pump chamber 218 and the first pump 207 is actuated to draw dialysate from the dialyzer (not shown) into the first pump chamber 208.

Finally, the second dialyzer inlet valve 217 and the second drain valve 211 are opened, the first and second dialyzer outlet valves 215, 213 and the first source valve 205 are closed and the first pump 207 is actuated to expel dialysate from the first pump chamber 208 into the drain 221 and operating the second pump 216 to expel dialysate from the second pump chamber 218 into the dialyzer (not shown). The operation of the third and fourth step is the same as the first and second except that the roles of the first and second pumps have been swapped over.

Second Mode of Operation—Hemodiafiltration (Split Pumping with Delay)

Alternatively, the second mode of operation of the arrangement 201 may begin with opening the first source valve 205 and the first drain valve 219, closing the first dialyzer outlet valve 215 and operating the second pump 216 to expel dialysate from the second pump chamber 218 into the drain 221 and operating the first pump 207 to draw dialysate into the first pump chamber 208 from the dialysate source 203.

In the second step, the first dialyzer inlet valve 209 is opened and the first dialyzer outlet valve 215, the first source valve 205 and the first drain valve 219 are closed. The first pump 207 is then actuated to expel dialysate from the first pump chamber 208 into the dialyzer and the second pump 216 is left idle. Thus, dialysate 327 in the first pump chamber 208 is forced under positive pressure into the dialyzer but as the dialyzer outlet valves 215, 213 are closed, the dialysate has nowhere else to go and so passes across the semipermeable membrane of the dialyzer and into the blood side of the dialyzer.

In the third step, the first dialyzer inlet valve 209 is closed, the first dialyzer outlet valve 215 is opened, the first pump 207 is left idle and the second pump 216 is actuated to draw dialysate from the dialyzer into the second pump chamber. The dialysate 327 drawn from the dialyzer is pulled from the patient's blood, across the semipermeable membrane of the dialyzer and into the second pump chamber 218.

The first, second and third steps are then repeated. In the fourth step. The second pump is operated to expel the dialysate 327 in the second pump chamber into the drain. Accordingly, after the fourth step, both pump chambers are empty.

In the fifth step, the second source valve 206 is opened and the first drain valve 211 and first dialysate outlet valve 213 are closed and the second pump 216 is operated to draw dialysate 327 from the dialysate source 203 into the second pump chamber 218. The second source valve 206 is the closed, the second dialyzer inlet valve 217 is opened and the pump is activated to expel the dialysate 327 in the second pump chamber 218 into the dialyzer.

In a sixth step, the second dialyzer inlet valve 217 is closed and the second dialyzer outlet valve 215 is opened and the first pump is operated to draw dialysate 327 from the dialyzer into the first pump chamber 208.

Finally, the second drain valve is opened and the first dialyzer inlet valve and second dialyzer outlet valve is closed and the dialysate is expelled from the first pump chamber into the drain.

The fifth, sixth and seventh method steps are then repeated thereby completing the pumping cycle.

Although the control system 500 has been described in the specific embodiment as a microprocessor, the control system 500 may instead comprise an electrical switching arrangement or a mechanical control arrangement. In the case of a mechanical control arrangement, rather than individual vacuum pumps for each platen cavity, it is envisaged that a single vacuum pump would apply a negative pressure to the platen and a mechanical camming or gearing arrangement would actuate valves on the platen to control the application of the negative/positive pressure selectively according to the required operating mode.

The invention claimed is:

1. A blood treatment device comprising:

a dialyzer;

a flow balance pump and valve arrangement, comprising:

a first pump operable to deliver a predetermined volume of cleaning solution from a cleaning solution source to the dialyzer or to remove the predetermined volume of cleaning solution from the dialyzer to a drain;

a second pump operable to deliver the predetermined volume of cleaning solution from the cleaning solution source to the dialyzer or to remove the predetermined volume of cleaning solution from the dialyzer to the drain;

a first dialyzer inlet valve arranged between the first pump and an inlet of the dialyzer;

a second dialyzer inlet valve arranged between the second pump and the inlet of the dialyzer;

a first dialyzer outlet valve arranged between an outlet of the dialyzer and the second pump;

a second dialyzer outlet valve arranged between the outlet of the dialyzer and the first pump;

a first cleaning solution source valve arranged between the cleaning solution source and the first pump;

a second cleaning solution source valve arranged between the cleaning solution source and the second pump;

a first drain valve arranged between the second pump and the drain;

a second drain valve arranged between the first pump and the drain; and each of the valves and the pumps of the flow balance pump and valve arrangement being independently operable; and a control system configured to operate the valves and pumps of the flow balance pump and valve arrangement in at least one first mode permitting hemodialysis and at least one second mode permitting hemodiafiltration;

wherein hemodialysis occurs because waste product from a patient's blood transfers to the cleaning solution via diffusion across a semi-permeable membrane in the dialyzer, but the cleaning solution substantially does not cross the membrane;

wherein hemodiafiltation occurs because the waste product from the patient's blood transfers to the cleaning solution when the cleaning solution is forced across the membrane into the patient's blood and then pulled back across the membrane; and wherein the at least one second mode includes operating the first pump and the second pump in phase to generate a positive pressure in the dialyzer, or operating the first pump and the second pump out of phase to generate a positive pressure in the dialyzer.

2. A device according to claim 1, wherein the control system is configured, in use, to alternate the operation of the valves and pumps between the at least one first mode and the at least one second mode.

3. A device according to claim 1, wherein the control system is configured to alternate the pump responsible for delivering cleaning solution to the dialyzer and the pump responsible for removing spent cleaning solution from the dialyzer after a given number of pumping cycles.

4. A device according to claim 3, wherein the number of pumping cycles is two or more pumping cycles.

5. A device according to claim 1, wherein the pumps are positive displacement pumps.

6. A device according to claim 5, wherein the pumps are membrane pumps.

7. A device according to claim 1, wherein the flow balance pump and valve arrangement is formed on a disposable cartridge.

8. A device according to claim 7, wherein the pumps and valves on the disposable cartridge are actuated by selective application of a negative or a positive air pressure thereto.

9. A device according to claim 8, wherein the selective application of the negative or the positive air pressure is effected by a pneumatic pump.

10. A device according to claim 9, wherein each pump or valve has an associated pneumatic pump on a machine which receives the cartridge.

11. A device according to claim 10, wherein the control system controls the operation of the respective pneumatic pumps.

12. A device according to claim 11, wherein the control system is a microprocessor which controls the pneumatic pumps electronically.

13. A device according to claim 12, wherein the control is effected wirelessly.

14. A method of operating the device according to claim 1, wherein the valves and pumps of the flow balance pump and valve arrangement are operated by the control system in the at least one first mode permitting hemodialysis and the at least one second mode permitting hemodiafiltration.

15. A method according to claim 14, wherein the valves and pumps are operated to alternate between the at least one first mode permitting hemodialysis and the at least one second mode permitting hemodiafiltration.

16. A method according to claim 14, wherein the valves and pumps are operated in the at least one second mode permitting hemodiafiltration by operating the first and second pumps in phase to generate a positive pressure in the dialyzer.

17. A method according to claim 14, wherein the at least one first mode comprises the steps of:

a) operating the first pump to draw the predetermined volume of cleaning solution from the cleaning solution source into the first pump and operating the second pump to expel the predetermined volume of spent cleaning solution from the second pump into the drain; and b) operating the first pump to expel the predetermined volume of cleaning solution from the first pump into the dialyzer and operating the second pump to draw the predetermined volume of spent cleaning solution from the dialyzer into the second pump.

18. A method according to claim 14, wherein the first mode comprises the steps of:

a) closing the first dialyzer inlet valve, closing the first dialyzer outlet valve, operating the first pump to draw the predetermined volume of cleaning solution from the cleaning solution source into the first pump and operating the second pump to expel the predetermined volume of cleaning solution from the second pump into the drain; and b) opening the first dialyzer inlet valve, opening the first dialyzer outlet valve, operating the first pump to expel the predetermined volume of cleaning solution from the first pump into the dialyzer and operating the second pump to draw the predetermined volume of cleaning solution from the dialyzer into the second pump.

19. A method according to claim 14, wherein the first mode comprises the steps of:

a) closing the first dialyzer inlet valve, closing the first dialyzer outlet valve, opening the first clean solution source valve, opening the first drain valve, operating the first pump to draw the predetermined volume of cleaning solution from the cleaning solution source into the first pump and operating the second pump to expel the predetermined volume of cleaning solution from the second pump into the drain; and b) opening the first dialyzer inlet valve, opening the first dialyzer outlet valve, closing the first clean solution source valve, closing the first drain valve, operating the first pump to expel the predetermined volume of cleaning solution from the first pump into the dialyzer and operating the second pump to draw the predetermined volume of cleaning solution from the dialyzer into the second pump.

20. A method according to claim 14, wherein the first mode comprises the steps of:

a) closing the first and second dialyzer inlet valves, closing the first and second dialyzer outlet valves, opening the first cleaning solution source valve, opening the first drain valve, closing the second cleaning solution source valve, closing the second drain valve, operating the first pump to draw the predetermined volume of cleaning solution from the cleaning solution source into the first pump and operating the second pump to expel the predetermined volume of cleaning solution from the second pump into the drain;

b) opening the first dialyzer inlet valve, opening the first dialyzer outlet valve, closing the first clean solution source valve, closing the first drain valve, operating the first pump to expel the predetermined volume of cleaning solution from the first pump into the dialyzer and operating the second pump to draw the predetermined volume of cleaning solution from the dialyzer into the second pump;

c) closing the first dialyzer inlet valve, closing the first dialyzer outlet valve, opening the first drain valve, and operating the second pump to expel the predetermined volume of cleaning solution from the second pump into the drain;

d) closing the first drain valve, opening the second cleaning solution source valve, and operating the second pump to draw the predetermined volume of cleaning solution from the clean solution source;

e) opening the second dialyzer inlet valve, opening the second dialyzer outlet valve, closing the second cleaning solution source valve, operating the second pump to expel the predetermined volume of cleaning solution from the second pump into the dialyzer and operating the first pump to draw the predetermined volume of cleaning solution from the dialyzer into the first pump; and f) closing the second dialyzer outlet valve, opening the second drain valve, closing the second dialyzer inlet valve, opening the second cleaning solution source valve, operating the second pump to draw the predetermined volume of cleaning solution from the cleaning solution source and operating the first pump to expel the predetermined volume of cleaning solution from the first pump into the drain.

21. A method according to claim 20, wherein the first mode further comprises repeating steps a) and b) one or more times before performing step c).

22. A method according to claim 20, wherein the first mode further comprises repeating steps e) and 0 one or more times.

23. A method according to claim 14, wherein the at least one second mode comprises the steps of:

a) operating the first pump to draw the cleaning solution from the cleaning solution source into the first pump and operating the second pump to draw the predetermined volume of cleaning solution from the dialyzer into the second pump; and b) operating the first pump to expel the predetermined volume of cleaning solution from the first pump into the dialyzer and operating the second pump to expel the predetermined volume of cleaning solution from the second pump into the drain.

24. A method according to claim 14, wherein the second mode comprises the steps of:

a) closing the first dialyzer inlet valve, opening the first dialyzer outlet valve, operating the first pump to draw the predetermined volume of cleaning solution from the cleaning solution source into the first pump and operating the second pump to draw the predetermined volume of cleaning solution from the dialyzer into the second pump; and b) opening the first dialyzer inlet valve, closing the first dialyzer outlet valve, operating the first pump to expel the predetermined volume of cleaning solution from the first pump into the dialyzer and operating the second pump to expel the predetermined volume of cleaning solution from the second pump into the drain.

25. A method according to claim 14, wherein the second mode comprises the steps of:

a) closing the first dialyzer inlet valve, opening the first dialyzer outlet valve, opening the first cleaning solution source valve, closing the first drain valve, operating the first pump to draw the predetermined volume of cleaning solution from the cleaning solution source into the first pump and operating the second pump to draw the predetermined volume of cleaning solution from the dialyzer into the second pump; and b) opening the first dialyzer inlet valve, closing the first dialyzer outlet valve, closing the first cleaning solution source valve, opening the first drain valve, operating the first pump to expel the predetermined volume of cleaning solution from the first pump into the dialyzer and operating the second pump to expel the predetermined volume of cleaning solution from the second pump into the drain.

26. A method according to claim 14, wherein the second mode comprises the steps of:

a) closing the first and second dialyzer inlet valves, opening the first dialyzer outlet valve, closing the second dialyzer outlet valve, opening the first cleaning solution source valve, closing the second cleaning solution source valve, closing the first and second drain valves, operating the first pump to draw the predetermined volume of cleaning solution from the cleaning solution source into the first pump and operating the second pump to draw the predetermined volume of cleaning solution from the dialyzer into the second pump;

b) opening the first dialyzer inlet valve, closing the first dialyzer outlet valve, closing the first cleaning solution source valve, opening the first drain valve, operating the first pump to expel the predetermined volume of cleaning solution from the first pump into the dialyzer and operating the second pump to expel the predetermined volume of cleaning solution from the second pump into the drain;

c) closing the first dialyzer inlet valve, opening the second dialyzer outlet valve, opening the second cleaning solution source valve, closing the first drain valve, operating the second pump to draw the predetermined volume of cleaning solution from the cleaning solution source into the second pump and operating the first pump to draw the predetermined volume of cleaning solution from the dialyzer into the first pump; and d) opening the second dialyzer inlet valve, closing the first and second dialyzer outlet valves, closing the first cleaning solution source valve, opening the second drain valve, operating the first pump to expel the predetermined volume of cleaning solution from the first pump into the drain and operating the second pump to expel the predetermined volume of cleaning solution from the second pump into the dialyzer.

27. A method according to claim 26, further comprising repeating steps a) and b) one or more times before performing step c).

28. A method according to claim 26, further comprising a step after step d) of repeating steps c) and d) one or more times.

29. A method according to claim 14, wherein the second mode comprises the steps of:

a) operating the first pump to draw the predetermined volume of cleaning solution from the cleaning solution source into the first pump and operating the second pump to expel the predetermined volume of cleaning solution from the second pump into the drain;

b) operating the first pump to expel the predetermined volume of cleaning solution from the first pump into the dialyzer; and c) operating the operating the second pump to draw the predetermined volume of cleaning solution from the dialyzer into the second pump.

30. A method according to claim 14, wherein the second mode comprises the steps of:

a) opening the first cleaning solution source valve, operating the first pump to draw the predetermined volume of cleaning solution from the cleaning solution source into the first pump and operating the second pump to expel the predetermined volume of cleaning solution from the second pump into the drain;

b) opening the first dialyzer inlet valve, operating the first pump to expel the predetermined volume of cleaning solution from the first pump into the dialyzer; and c) closing the first dialyzer inlet valve, opening the first dialyzer outlet valve, operating the second pump to draw the predetermined volume of cleaning solution from the dialyzer into the second pump.

31. A method according to claim 14, wherein the second mode comprises the steps of:

a) closing the first dialyzer outlet valve, opening the first cleaning solution source valve, opening the first drain valve, operating the first pump to draw the predetermined volume of cleaning solution from the cleaning solution source into the first pump and operating the second pump to expel the predetermined volume of cleaning solution from the second pump into the drain;

b) opening the first dialyzer inlet valve, closing the first cleaning solution source valve, and operating the first pump to expel the predetermined volume of cleaning solution from the first pump into the dialyzer; and c) closing the first dialyzer inlet valve, opening the first dialyzer outlet valve, closing the first drain valve, and operating the second pump to draw the predetermined volume of cleaning solution from the dialyzer into the second pump.

32. A method according to claim 14, wherein the second mode comprises the steps of:

a) closing the first dialyzer outlet valve, opening the first cleaning solution source valve, opening the first drain valve, operating the first pump to draw the predetermined volume of cleaning solution from the cleaning solution source into the first pump and operating the second pump to expel the predetermined volume of cleaning solution from the second pump into the drain;

b) opening the first dialyzer inlet valve, closing the first cleaning solution source valve, and operating the first pump to expel the predetermined volume of cleaning solution from the first pump into the dialyzer;

c) closing the first dialyzer inlet valve, opening the first dialyzer outlet valve, closing the first drain valve, and operating the second pump to draw the predetermined volume of cleaning solution from the dialyzer into the second pump;

d) opening the first drain valve, closing the first dialyzer outlet valve, and operating the second pump to expel the cleaning solution from the second pump into the drain;

e) closing the first drain valve, opening the second source valve, closing the second dialyzer inlet valve and operating the second pump to draw a predetermined volume cleaning solution from the cleaning solution source into the second pump;

f) closing the second source valve, opening the second dialyzer inlet valve and operating the second pump to expel the predetermined volume of cleaning solution from the second pump into the dialyzer;

g) closing the second dialyzer inlet, opening the second dialyzer outlet, closing the second drain valve and operating the first pump to draw the predetermined volume of cleaning solution into the first pump; and h) opening the second drain valve, closing the second dialyzer outlet valve, opening the second source valve and operating the first pump to expel the predetermined volume of cleaning solution from the first pump into the drain and operating the second pump to draw the predetermined volume of cleaning solution from the cleaning solution source into the second pump.

33. A method according to claim 32, further comprising repeating steps a) to c) one or more times before performing step d).

34. A method according to claim 32, further comprising a step after step h) of repeating steps f) to h) one or more times.

35. A method according to claim 14, wherein the second mode comprises the steps of:

a) operating both the first and second pumps to draw the predetermined volume of cleaning solution from the cleaning solution source into each of the first and second pumps;

b) operating both the first and second pumps to expel the predetermined volume of cleaning solution from each of the first and second pumps into the dialyzer and across the membrane of the dialyzer;

c) operating the first and second pumps to draw the predetermined volume of cleaning solution from the dialyzer into each of the first and second pumps; and d) operating both the first and second pumps to expel the predetermined volume of cleaning solution from each of the first and second pumps into the drain.

36. A method according to claim 14, wherein the second mode comprises:

a) opening the first and second cleaning solution source valves and the first and second dialyzer inlet valves, closing the first and second dialyzer outlet valves and the first and second drain valves and operating the first and second pumps to draw the predetermined volume of cleaning solution from the cleaning solution source into each of the first and second pumps;

b) closing the first and second source valves and the first and second dialyzer outlet valves, opening the first and second dialyzer inlet valves and operating both the first and second pumps to expel the predetermined volume of cleaning solution from each of the first and second pumps into the dialyzer;

c) opening the first and second dialyzer outlet valves, closing the first and second dialyzer inlet valves and operating both the first and second pumps to draw the predetermined volume of cleaning solution from the dialyzer into each of the first and second pumps; and d) opening the first and second drain valves, closing the first and second dialyzer outlet valves and operating both the first and second pumps to expel the predetermined volume of cleaning solution from each of the first and second pumps into the drain.

37. The method according to claim 14, wherein the valves and pumps are operated in the at least one second mode permitting hemodiafiltration by operating the first and second pumps out of phase to generate a positive pressure in the dialyzer.

*38. A blood treatment device comprising:*

*a dialyzer;*

*a first pump configured to deliver a cleaning solution to, and remove the cleaning solution from, the dialyzer;*

*a second pump configured to deliver the cleaning solution to, and remove the cleaning solution from, the dialyzer; and*

*a control system configured to operate one or more valves, the first pump, and the second pump in at least one first mode permitting hemodialysis and at least one second mode permitting hemodiafiltration, wherein the at least one second mode permitting hemodiafiltration includes transferring waste product from blood of a patient to the cleaning solution as the cleaning solution is forced across a semi-permeable membrane of the dialyzer and into the blood of the patient and then pulled back across the semi-permeable membrane, and the control system operates the first pump and the second pump out of phase with one another or in phase with one another such that a positive pressure is generated in the dialyzer in the at least one second mode permitting hemodiafiltration.*

*39. The blood treatment device of claim 38, wherein the control system operates the one or more valves, the first pump, and the second pump to alternate between the at least one first mode permitting hemodialysis and the at least one second mode permitting hemodiafiltration.*

*40. The blood treatment device of claim 38, further comprising the one or more valves.*

*41. The blood treatment device of claim 38, wherein the one or more valves comprise at least one of a first dialyzer inlet valve, a second dialyzer inlet valve, a first dialyzer outlet valve, a second dialyzer outlet valve, a first cleaning solution source valve, a second cleaning solution source valve, a first drain valve, and a second drain valve.*

*42. The blood treatment device of claim 38, wherein the one or more valves comprise at least two of a first dialyzer inlet valve, a second dialyzer inlet valve, a first dialyzer outlet valve, a second dialyzer outlet valve, a first cleaning solution source valve, a second cleaning solution source valve, a first drain valve, and a second drain valve.*

*43. The blood treatment device of claim 38, wherein the one or more valves comprise a first dialyzer inlet valve, a second dialyzer inlet valve, a first dialyzer outlet valve, a second dialyzer outlet valve, a first cleaning solution source valve, a second cleaning solution source valve, a first drain valve, and a second drain valve.*

*44. The blood treatment device of claim 38, wherein the first pump is operable to deliver and remove a predetermined volume of cleaning solution to and from the dialyzer.*

*45. The blood treatment device of claim 38, wherein the second pump is operable to deliver and remove a predetermined volume of cleaning solution to and from the dialyzer.*

* * * * *